United States Patent
Van Voorhees et al.

(10) Patent No.: US 12,246,169 B2
(45) Date of Patent: Mar. 11, 2025

(54) MEDICAL DELIVERY DEVICES HAVING LOW LUBRICANT HYDROPHOBIC SYRINGE BARRELS

(71) Applicant: W.L. Gore & Associates, Inc., Newark, DE (US)

(72) Inventors: Eric J. Van Voorhees, Landenberg, PA (US); Benjamin Wright, Elkton, MD (US)

(73) Assignee: W.L. Gore & Associates, Inc., Newark, DE (US)

( * ) Notice: Subject to any disclaimer, the term of this patent is extended or adjusted under 35 U.S.C. 154(b) by 1187 days.

(21) Appl. No.: 16/975,433

(22) PCT Filed: Feb. 26, 2019

(86) PCT No.: PCT/US2019/019570
§ 371 (c)(1),
(2) Date: Aug. 25, 2020

(87) PCT Pub. No.: WO2019/173083
PCT Pub. Date: Sep. 12, 2019

(65) Prior Publication Data
US 2021/0030970 A1 Feb. 4, 2021

Related U.S. Application Data

(60) Provisional application No. 62/639,317, filed on Mar. 6, 2018.

(51) Int. Cl.
*A61M 5/315* (2006.01)
*A61M 5/20* (2006.01)
*A61M 5/31* (2006.01)

(52) U.S. Cl.
CPC .......... *A61M 5/31513* (2013.01); *A61M 5/20* (2013.01); *A61M 5/3129* (2013.01);
(Continued)

(58) Field of Classification Search
CPC .......... A61M 5/31511; A61M 5/31513; A61M 5/315; A61M 5/31505; A61M 2005/3101;
(Continued)

(56) References Cited

U.S. PATENT DOCUMENTS 4,303,070 A * 12/1981 Ichikawa .......... A61M 5/31513
604/222
5,374,473 A 12/1994 Knox et al.
(Continued)

FOREIGN PATENT DOCUMENTS

EP 0026940 5/1984
JP 201789528 10/2017
(Continued)

OTHER PUBLICATIONS

"What is contact angle?" www.brighton-science.com/what-is-contact-angle (accessed Aug. 1, 2024) (Year: 2024).*
(Continued)

*Primary Examiner* — Nathan R Price
*Assistant Examiner* — Adam J. Cermak
(74) *Attorney, Agent, or Firm* — Faegre Drinker Biddle & Reath LLP

(57) ABSTRACT

The present disclosure relates to medical delivery devices that include a barrel having an inner surface that is hydrophobic. The medical delivery device includes a barrel with a hydrophobic inner surface and a stopper that can provide air and liquid impermeability while also possessing on or more of: a low break loose force, a low average glide force, and a low glide force variation. The contact angle of the inner surface of the barrel is greater than 90°.

16 Claims, 7 Drawing Sheets

(52) U.S. Cl.
CPC ............. *A61M 2005/3131* (2013.01); *A61M 2205/0216* (2013.01); *A61M 2205/0222* (2013.01); *A61M 2205/0238* (2013.01)

(58) Field of Classification Search
CPC .......... A61M 2005/31506; A61M 2005/3131; A61M 2205/0216; A61M 2205/0222; A61M 2205/0238; A61M 5/3205; A61M 5/3129; A61L 31/048
See application file for complete search history.

(56) References Cited

U.S. PATENT DOCUMENTS

| | | | | |
|---|---|---|---|---|
| 5,586,975 | A | * | 12/1996 | Tanaka ............... A61M 5/31513 604/218 |
| 5,708,044 | A | | 1/1998 | Branca |
| 5,792,525 | A | | 8/1998 | Fuhr et al. |
| 6,030,694 | A | | 2/2000 | Dolan et al. |
| 6,090,081 | A | * | 7/2000 | Sudo ..................... B29C 39/20 604/218 |
| 6,541,589 | B1 | | 4/2003 | Baillie |
| 7,521,010 | B2 | | 4/2009 | Kennedy |
| 7,531,611 | B2 | | 5/2009 | Sabol et al. |
| 8,637,144 | B2 | | 1/2014 | Ford |
| 8,658,707 | B2 | | 2/2014 | Xu et al. |
| 8,722,178 | B2 | * | 5/2014 | Ashmead ............ A61M 5/3202 428/521 |
| 9,139,669 | B2 | | 9/2015 | Xu et al. |
| 9,441,088 | B2 | | 9/2016 | Sbriglia et al. |
| 9,597,458 | B2 | | 8/2017 | Ashmead et al. |
| 9,732,184 | B2 | | 8/2017 | Sbriglia et al. |
| 9,926,416 | B2 | | 3/2018 | Sbriglia |
| 10,471,211 | B2 | * | 11/2019 | Rusch ................. A61M 5/3129 |
| 2003/0023206 | A1 | * | 1/2003 | Bausmith, III ....... A61M 5/007 604/218 |
| 2010/0298738 | A1 | * | 11/2010 | Felts ..................... C23C 16/505 118/712 |
| 2011/0137263 | A1 | * | 6/2011 | Ashmead ............ A61M 5/3202 604/230 |
| 2011/0313363 | A1 | * | 12/2011 | D'Souza ................ A61L 29/14 427/2.28 |
| 2012/0123345 | A1 | * | 5/2012 | Felts ................... A61M 5/3129 604/403 |
| 2012/0251748 | A1 | * | 10/2012 | Ashmead .......... A61M 5/31513 428/218 |
| 2012/0252709 | A1 | * | 10/2012 | Felts ................... A61M 5/3129 508/100 |
| 2013/0197451 | A1 | * | 8/2013 | Ishii ......................... B32B 27/00 604/221 |
| 2013/0200549 | A1 | * | 8/2013 | Felts ................... A61M 5/3134 264/275 |
| 2014/0212612 | A1 | | 7/2014 | Sbriglia |
| 2014/0303567 | A1 | * | 10/2014 | Qurishi ................. A61M 5/281 604/218 |
| 2015/0021339 | A1 | * | 1/2015 | Felts ....................... C23C 16/36 220/626 |
| 2015/0098084 | A1 | * | 4/2015 | Felts ....................... C23C 16/50 356/432 |
| 2015/0126941 | A1 | * | 5/2015 | Felts ......................... A61J 1/00 604/230 |
| 2015/0148751 | A1 | * | 5/2015 | Yotsutsuji ......... A61M 5/31513 604/218 |
| 2015/0297800 | A1 | * | 10/2015 | Weikart .................... A61J 1/05 422/430 |
| 2016/0022918 | A1 | * | 1/2016 | Gunzel .................. B32B 27/08 604/222 |
| 2016/0032044 | A1 | | 2/2016 | Sbriglia et al. |
| 2016/0032069 | A1 | | 2/2016 | Sbriglia |
| 2016/0032071 | A1 | | 2/2016 | Sbriglia et al. |
| 2017/0203043 | A1 | * | 7/2017 | Rusch ............... A61M 5/31513 |
| 2017/0296752 | A1 | * | 10/2017 | Masuyama ....... A61M 5/31513 |
| 2017/0296756 | A1 | * | 10/2017 | Giraud ................... A61L 31/14 |
| 2019/0000919 | A1 | * | 1/2019 | Brockmeyer .......... A61P 27/02 |
| 2019/0352778 | A1 | * | 11/2019 | Felts ................. A61M 5/31513 |

FOREIGN PATENT DOCUMENTS

| | | | |
|---|---|---|---|
| WO | WO94/13469 | 6/1994 | |
| WO | WO-2012006555 A1 * | 1/2012 | ............. A61M 5/19 |
| WO | WO-2013064590 A1 * | 5/2013 | ............ A61M 5/281 |
| WO | WO-2015/054282 | 4/2014 | |
| WO | WO-2015054282 A2 * | 4/2015 | ........... A61L 31/049 |
| WO | WO-2017087798 A1 * | 5/2017 | ........... A61K 38/179 |
| WO | WO-2017/123840 | 7/2017 | |

OTHER PUBLICATIONS

International Standard ISO 11040-4, Prefilled syringes Part 4: Glass barrels for injectables and sterilized subassembled syringes ready for filling.

Ville Jokinen et al; Biomicrofluidics, Oxygen and nitrogen plasma hydrophilization and hydrophobic recovery of polymers, vol. 6, Issue 1 (2012).

* cited by examiner

MEDICAL DELIVERY DEVICES HAVING LOW LUBRICANT HYDROPHOBIC SYRINGE BARRELS

FIELD

The present invention relates to medical delivery devices with low lubricant, hydrophobic barrels, and in particular, to medical delivery devices containing a stopper that enables high levels of air and liquid impermeability and at least one of: a low break loose force, a low average glide force, and low glide force variation where the barrel is free or substantially free of silicone.

BACKGROUND

Medical delivery devices such as syringes, auto-injectors, and pens typically include a barrel, a stopper positioned within the barrel, and a plunger rod or actuation mechanism to displace the stopper. The stopper is typically air and liquid impermeable while also possessing low-friction slidability. Air and liquid impermeability is important for eliminating liquid leakage within the barrel and the introduction of air between an outer face of the stopper and an inner wall of the barrel when charging or discharging the liquid inside the medical delivery device. Low-friction slidability is important for facilitating the charging and discharging of the liquid inside the medical delivery device. In addition to these requirements, a medical syringe, auto-injector, or pen should not adversely affect any pharmaceutical composition such as biopharmaceuticals that come in contact with the syringe (e.g., a pre-filled syringe, auto-injector, or pen comprising a pharmaceutical composition).

Accordingly, a need exists for stoppers covered with a fluoropolymer or non-fluoropolymer film or laminate that when used in conjunction with hydrophobic glass or resin barrels are able to achieve high levels of air and liquid impermeability while also achieving a low break loose force, a low average glide force, and a low glide force variation.

SUMMARY

The present disclosure relates to a medical delivery device having a barrel with a hydrophobic inner surface and a stopper that can provide air and liquid impermeability while also possessing one or more of: a low break loose force, a low average glide force, and a low glide force variation.

One embodiment relates to a medical delivery device that includes a barrel and a stopper contacting at least a portion of the inner surface of the barrel. The inner surface of the barrel is hydrophobic. The surface energy of the barrel portion that is in contact with the stopper is such that the water contact angle is above 90°. The stopper has a glide force variation less than about 1.3 N when calculated according to the Glide Force Variation test method described herein. In some embodiments, the stopper has an average glide force less than about 4 N. In addition, the stopper further includes a sliding surface that is less than about 2.0 mm measured at a compressibility from about 4.5% to about 7.9%. Additionally, the stopper may have a break loose force of less than about 7.0 N.

A second embodiment relates to a medical delivery device that includes a barrel and a stopper contacting at least a portion of the inner surface of the barrel. The inner surface of the barrel is hydrophobic. The surface energy of the barrel portion that is in contact with the stopper is such that the water contact angle is above 90°. The stopper has a glide force variation less than about 1.3 N when calculated according to the Glide Force Variation test method described herein. In some embodiments, the stopper has an average glide force less than about 7 N. In addition, the stopper further includes a sliding surface from about 2.0 mm to about 3.2 mm measured at a compressibility from about 4.5% to about 7.9%. Additionally, the stopper may have a break loose force from about 4.0 N to about 10 N.

A third embodiment relates to a medical delivery device that includes a barrel and a stopper contacting at least a portion of the inner surface of the barrel. The inner surface of the barrel is hydrophobic. The surface energy of the barrel portion that is in contact with the stopper is such that the water contact angle is above 90°. The stopper has a glide force variation less than about 1.3 N when calculated according to the Glide Force Variation test method described herein. In some embodiments, the stopper has an average glide force less than about 13 N. In addition, the stopper further includes a sliding surface greater than about 2.0 mm measured at a compressibility from about 7.0% to about 17.0%. Additionally, the stopper may have a break loose force from about 6.0 N to about 20 N.

A fourth embodiment relates to a medical delivery device that includes a barrel and a stopper contacting at least a portion of the inner surface of the barrel. The inner surface of the barrel is hydrophobic. The surface energy of the barrel portion that is in contact with the stopper is such that the water contact angle is above 90°. The stopper has a glide force variation less than about 1.3 N when calculated according to the Glide Force Variation test method described herein. In addition, the stopper further includes a sliding surface less than about 2.0 mm measured at a compressibility from about 7.0% to about 17%. Additionally, the stopper may have a break loose force from about 2.0 N to about 13 N.

DESCRIPTION OF DRAWINGS:

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
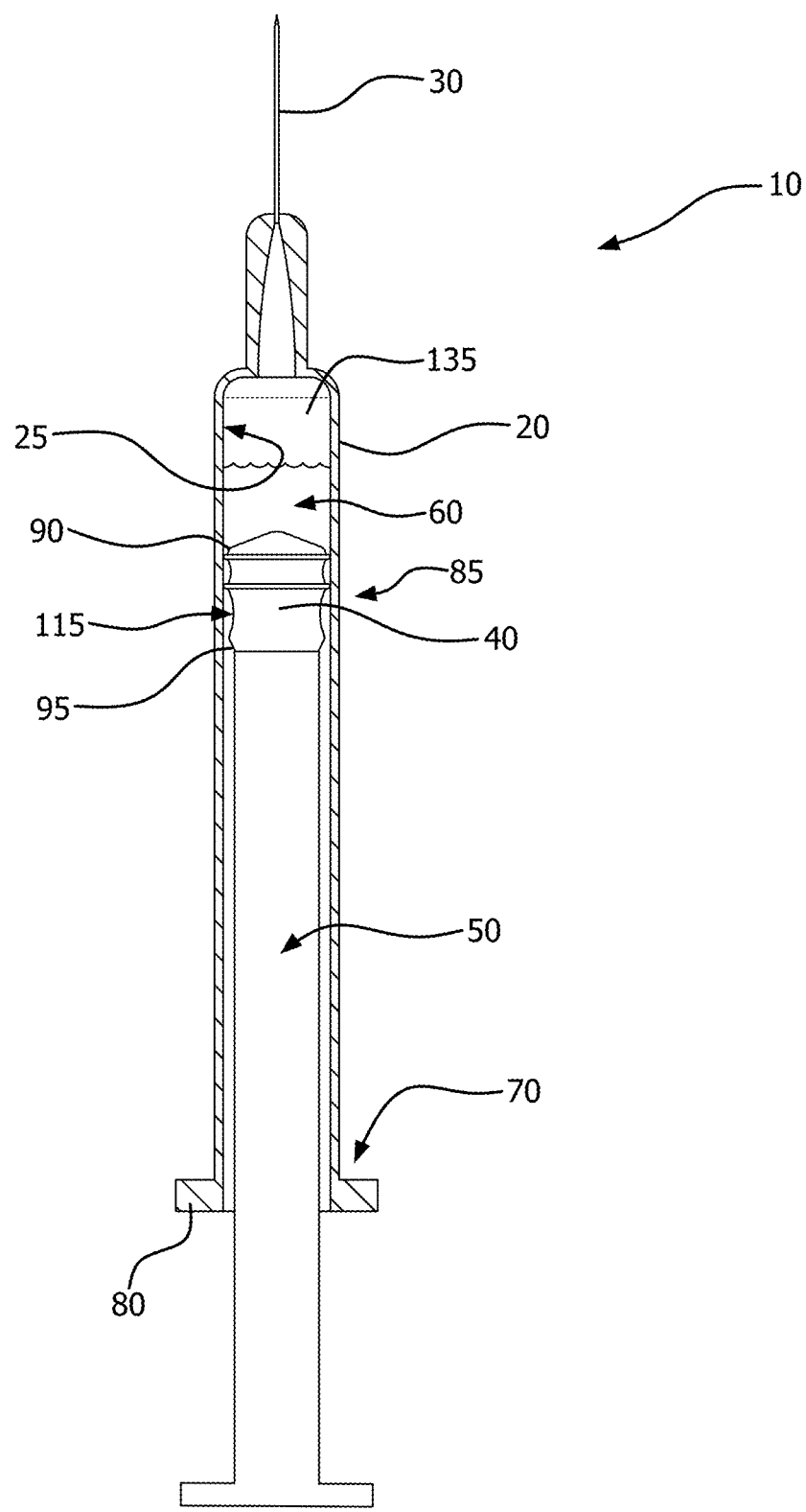
FIG. 1 is a schematic illustration of a cross section of a syringe in accordance with some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the figures should not be construed as limiting. As used herein, the terms "silicone" and "silicone oil" may be used interchangeably herein.

The present disclosure is directed to medical delivery devices (e.g., syringes, auto-injectors, and pens) that include a stopper at least partially covered with a fluoropolymer (or non-fluoropolymer) film or fluoropolymer (or non-fluoropolymer) laminate, a barrel, and a plunger rod or actuation mechanism to displace the stopper within the barrel. The barrel provides a hydrophobic inner surface that in combination with the fluoropolymer (or non-fluoropolymer) laminate (or fluoropolymer or non-fluoropolymer film) achieve high levels of air and liquid impermeability while also maintaining acceptably low break loose force, low average glide force, and low glide force variation.

The stoppers described herein may be used in syringes, auto-injectors, and pens for storing and delivering a fluid, typically for medical use. In some embodiments, the syringe may be pre-filled with a therapeutic (e.g., a pre-filled syringe). In at least one embodiment, the syringes, auto-injectors, or pens contain a therapeutic that treats diseases, such as, but not limited to, ocular disease (e.g., macular degeneration and glaucoma) or diabetes. Advantageously, the stoppers and barrels do not contain silicone, silicone oil, or any other liquid lubricant. Thus, the barrels in the medical devices described herein are free or substantially free of silicone and silicone oil (or other liquid lubricant). As used herein, the term "substantially free" is meant to denote an unquantifiable or trace amount of the identified substance (e.g., silicone, silicone oil, or other lubricant).

The stopper may be at least partially covered with a fluoropolymer film, such as a polytetrafluoroethylene (PTFE) film or a densified expanded polytetrafluoroethylene (ePTFE) film. Films based on PTFE or ePTFE provide thin and strong barrier layers to leachables and extractables that may be present in the elastomer and might otherwise contaminate the therapeutic liquid in the barrel. The superior strength of the expanded fluoropolymer structure allows these materials to form thin barriers, which remain intact during the forming process and installation of the stopper into the syringe barrel. Additionally, the use of at least partially porous and advantageously fibrilizing materials such as PTFE in combination with other materials provides numerous advantages. For example, the use of such porous materials may provide a scaffold that enables thin strong barrier layers to be made and improves the bond between the elastomer and the laminate.

Alternatively, the stopper may be at least partially covered with a laminate. The laminate may have a single layer or multiple layer construction. Laminate compliance with the stopper is beneficial to maintaining a seal between the stopper and the barrel. Porous materials such as ePTFE provide improved compliance with the stopper. Improved compliance may result from reduced film thickness, flexural compliance, and/or the compressibility of one or more layers of the porous material. Accordingly, by providing a laminate that is at least partially porous to the outside (e.g. the external or outermost surface) of the stopper, the seal between the stopper and syringe barrel may be improved while the sliding force is reduced.

Turning to FIG. 1, FIG. 1 depicts a syringe 10 in accordance with some embodiments. The syringe 10 includes a lubricant-free barrel 20 with an inner surface 25, a piercing element 30 for injecting therapeutics, a stopper 40 that may be integral with a plunger rod 50, and a receiving chamber 60. The stopper 40 is attached to the proximal end 85 of the plunger rod 50 and contacts at least a portion of the inner surface 25 of the barrel. The inner surface 25 has a surface energy and a water contact angle, as is discussed below. The proximal end 70 of the barrel 20 may include a flange 80 to be used as a finger stopper for pressing and pulling the plunger rod 50. In addition, stopper 40 includes opposed proximal and distal ends 90, 95 respectively, and a side surface 115 extending therebetween. The side surface 115 of stopper 50 may include two or more ribs such as one or more circumferentially extending annular ribs. It is within the scope of the invention that stopper 40 may contain ribs and/or be one in accordance with FIGS. 3-10 described below, or it may be a stopper without ribs.

It is to be appreciated that the piercing element 30 may include a sharply pointed needle cannulae, or a blunt-ended cannula, such as those employed with "needleless" systems. For ease of illustration, the piercing element 30 depicted and described herein is a sharply pointed, elongate needle cannula 30 with a sharply pointed distal end FIG. 1 also depicts a material 135 provided in the receiving chamber 30 of barrel 20 (e.g., a prefilled syringe). For purposes of illustration but not of limitation, the material 135 is herein identified as a predetermined dose of a pharmaceutical composition 135. However, it should be understood that the material 135 could be any type of liquid or material capable of being expelled from a syringe, or the material 135 may be all together absent from the receiving chamber, such as in an unfilled syringe.

Figure 2:
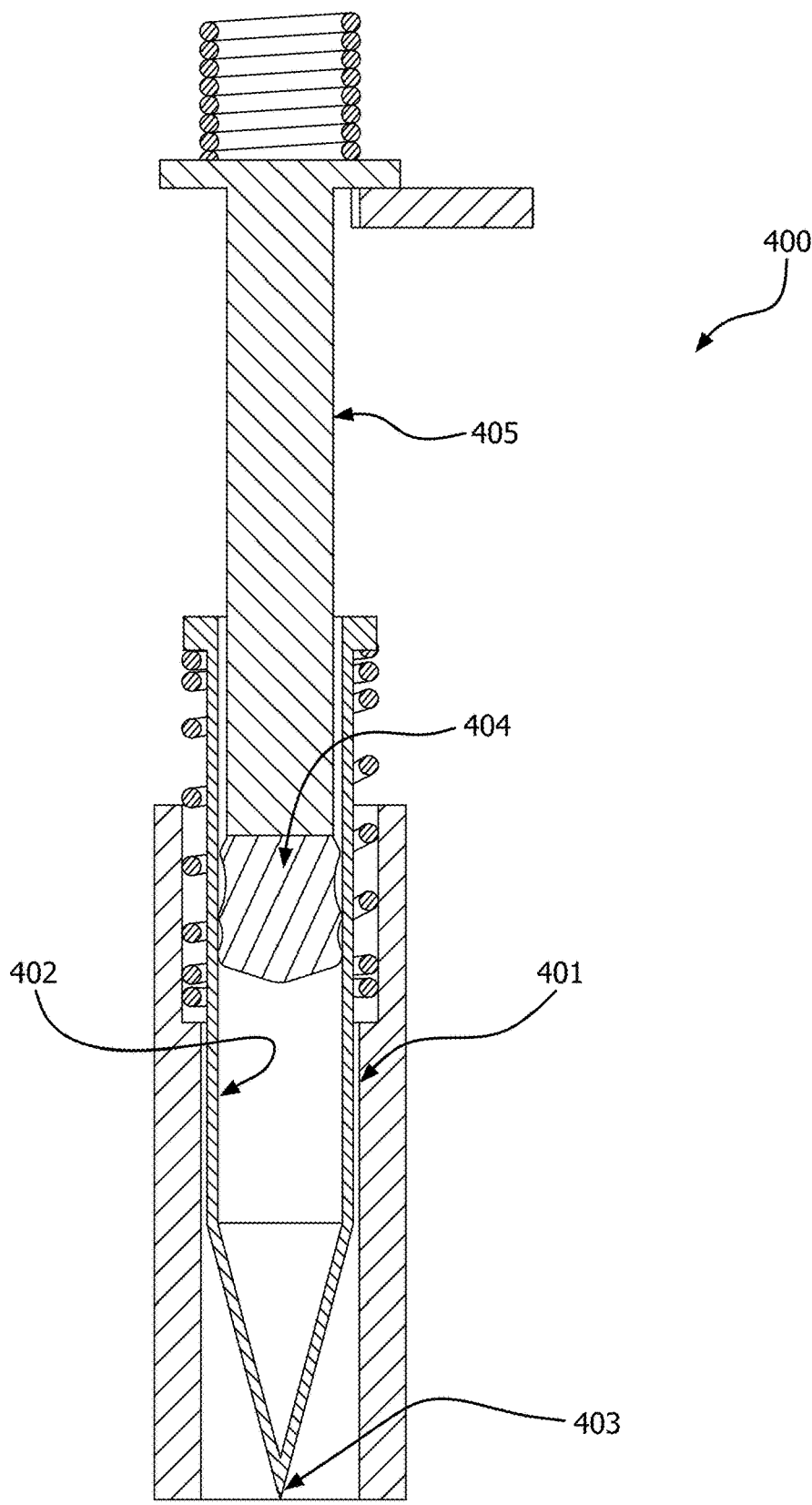
FIG. 2 is schematic cross section of an auto-injector in accordance with some embodiments.

FIG. 2 shows an auto-injector 400 in accordance with some embodiments. The auto-injector 400 includes a barrel 401, an injection member 403 for injecting therapeutics, and a stopper 404. The stopper 404 may be integral with a plunger rod 405. The barrel 401 is lubricant-free. The inner surface 402 of the barrel 401 has a surface energy and a water contact angle. It is within the scope of the invention that stopper 404 may include ribs and/or a stopper as depicted and described with respect to FIGS. 3-10, or it may be a stopper without ribs. The auto-injector 400 may incorporate a variable actuation force applied to the stopper 404. The elution rate of the drug through the auto-injector is directly proportional to this applied force.

The stoppers 40, 404 may be formed of an elastomeric body 125. The elastomeric body 125 may include any suitable elastomer, such as, for example, rubbers constructed from butyl, bromobutyl, chlorobutyl, silicone, nitrile, styrene butadiene, polychloroprene, ethylene propylene diene, fluoroelastomers, thermoplastic elastomers (TPE), thermoplastic vulcanizates (TPV), materials sold under the trade name VITON®, and combinations and blends thereof. Exemplary elastomeric materials include, but are not limited to, butyl rubber, bromobutyl rubber, chlorobutyl rubber, silicone, nitrile, styrene butadiene, polychloroprene, ethylene propylene diene, fluoroelastomers and combinations thereof. In some embodiments, the elastomeric body 125 may have an initial modulus (small strain) of between about 2.5 MPa to about 5 MPa, or between about 3 MPa to about 4 MPa. In one non-limiting embodiment, the initial modulus may be, for example, about 3.5 MPa (plus/minus measurement and variability tolerance). The materials of the film and/or laminate layers that cover the stopper are chosen, as described in detail herein, to provide, for example, a low coefficient of friction, compliance, low extractables and leachables, and good barrier properties as they relate to extractables and leachables from the elastomeric body 125, as well as good air and liquid impermeability.

Figure 3:
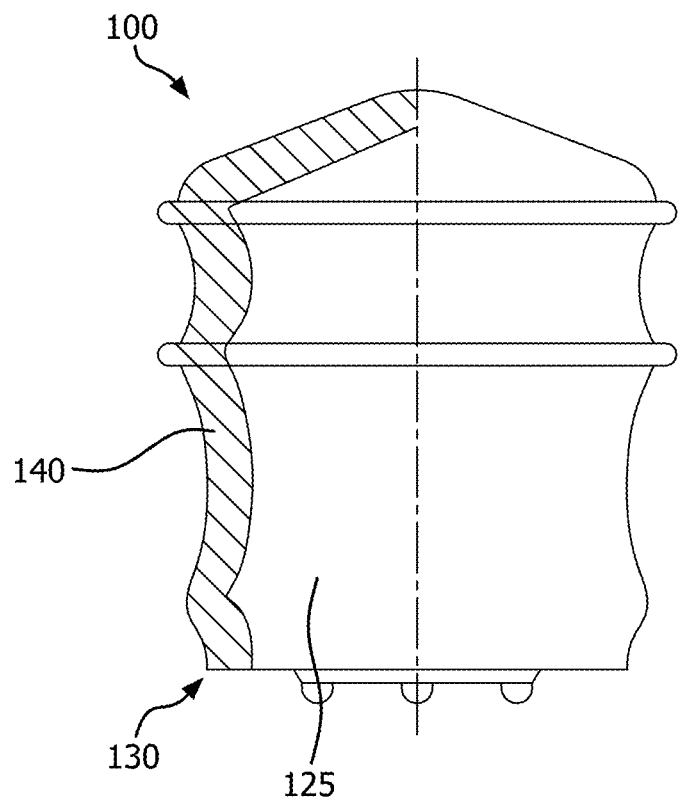
FIGS. 3-10 are schematic illustrations of cross-sectional side views of stoppers depicting varying types of laminates in accordance with some embodiments.

In some embodiments, the stoppers 40, 404 may be formed of an elastomeric body 125 and one or more laminate layer 130. The laminate layer 130 may include a single layer of a polymer barrier layer 140. FIG. 3 depicts such a stopper 100 that includes an elastomeric body 125 and a single barrier layer 140. In some embodiments, the barrier layer 140 may include, or be formed of, an expanded fluoropolymer or a densified expanded fluoropolymer, preferably an expanded polytetrafluoroethylene (ePTFE) or a densified expanded polytetrafluoroethylene. Other suitable fluoropolymers for use in or as the barrier layer 140 include, but are not limited to, fluorinated ethylene propylene (FEP), polyvinylidene fluoride, polyvinylfluoride, perfluoropropylvinylether, perfluoroalkoxy polymers, tetrafluoroethylene (TFE), Parylene AF-4, Parylene VT-4, and copolymers and combinations thereof. Non-fluoropolymers such as, but not limited to, polyethylene, polypropylene, Parylene C, and Parylene N may also or alternatively be used to form the barrier layer 140.

A densified ePTFE film may be prepared in the manner described in U.S. Pat. No. 7,521,010 to Kennedy, et al., U.S. Pat. No. 6,030,694 to Dolan et al., U.S. Pat. No. 5,792,525 to Fuhr et al., or U.S. Pat. No. 5,374,473 to Knox et al. Expanded copolymers of PTFE, such as are described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu et al. may also or alternatively be utilized, particularly if they are densified.

In one or more embodiment, the barrier layer 140 may include, or be formed of, one or more of the following materials: ultra-high molecular weight polyethylene as taught in U.S. Pat. No. 9,926,416 to Sbriglia; polyparaxylylene as taught in U.S. Patent Publication No. 2016/0032069 to Sbriglia; polylactic acid as taught in U.S. Pat. No. 9,732,184 to Sbriglia, et al.; and/or VDF-co-(TFE or TrFE) polymers as taught in U.S. Pat. No. 9,441,088 to Sbriglia.

The barrier layer 140 may also include an expanded polymeric material including a functional tetrafluoroethylene (TFE) copolymer material having a microstructure characterized by nodes interconnected by fibrils, where the functional TFE copolymer material includes a functional copolymer of TFE and PSVE (perfluorosulfonyl vinyl ether), or TFE with another suitable functional monomer, such as, but not limited to, vinylidene fluoride (VDF), vinyl acetate, or vinyl alcohol. The functional TFE copolymer material may be prepared, for example, according to the methods described in U.S. Pat. No. 9,139,669 to Xu et al. or U.S. Pat. No. 8,658,707 to Xu et al.

Figure 4:
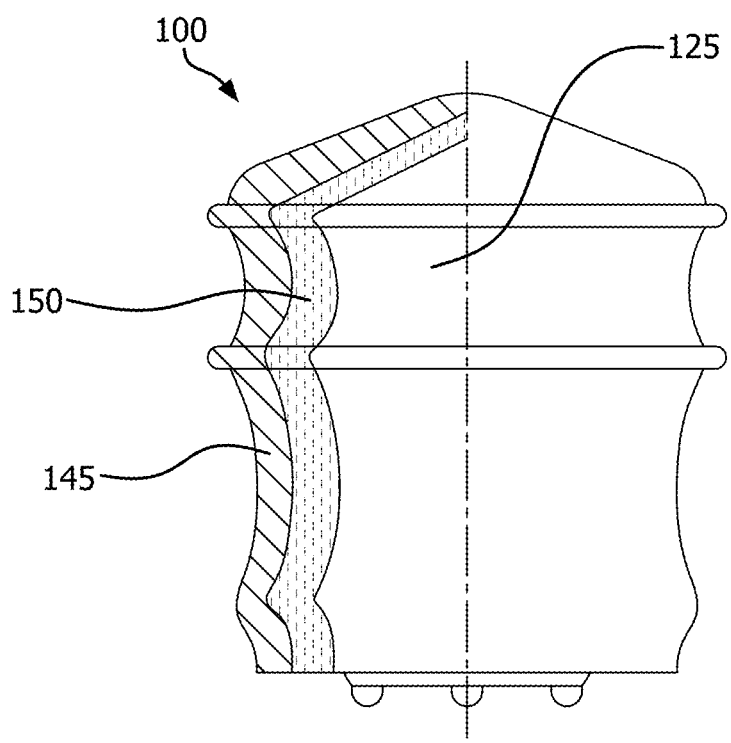

In another embodiment shown in FIG. 4, the laminate layer 130 includes a composite material that contains a barrier layer 145 and a porous layer 150. It is to be appreciated that any of the materials (e.g., fluoropolymers and non-fluoropolymers) set forth above with respect to the barrier layer 140 may be used in or as the barrier layer 145. The porous layer 150 may include expanded polytetrafluoroethylene (for example, ePTFE as taught in U.S. Pat. No. 6,541,589 to Baille) or other porous expanded (and often fibrilizing) fluoropolymers. The laminate layer 130 that contains the barrier layer 145 and the porous layer 150 may be constructed by coating or otherwise depositing the barrier polymer (e.g. fluoropolymer) onto the porous layer 150 to create the composite material. One such example is to deposit a granular or powdered fluoropolymer such as powdered polytetrafluoroethylene onto the surface of a porous ePTFE layer in a coating process. The ePTFE layer should be constructed to be sufficiently thermally stable to allow heat treatment of the deposited granular or powdered fluoropolymer for the creation of a barrier layer or for the bonding of the deposited barrier layer to the porous ePTFE layer. It is to be noted that the porous (e.g., ePTFE) layer may be filled with an organic or inorganic material to provide color, lubricity, or other functional attributes.

Figure 5:
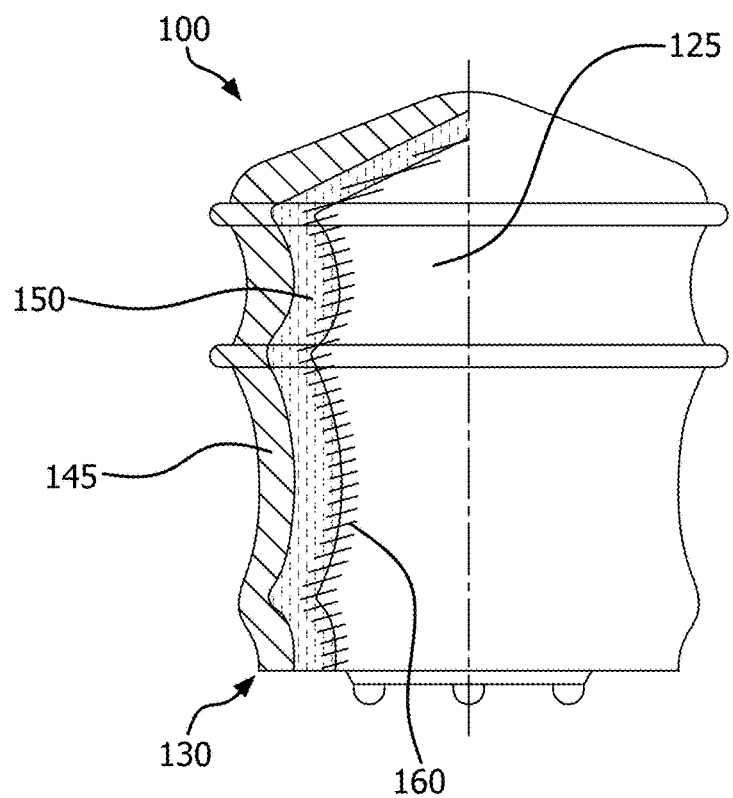

In accordance with some embodiments, the elastomer material of the elastomeric body 125 may at least partially penetrate the porous layer 150. FIG. 5 illustrates a cross-section of a stopper 100 depicting the barrier layer 145, the porous layer 150, and the elastomeric body 125. Specifically, FIG. 5 shows a region of partial penetration 160 of the elastomer material of the elastomeric body 125 into the porous layer 150. Penetration of the elastomer material of the elastomeric body 125 into the porous layer 150 improves the bond between the elastomeric body 125 and the laminate layers 130.

Figure 6:
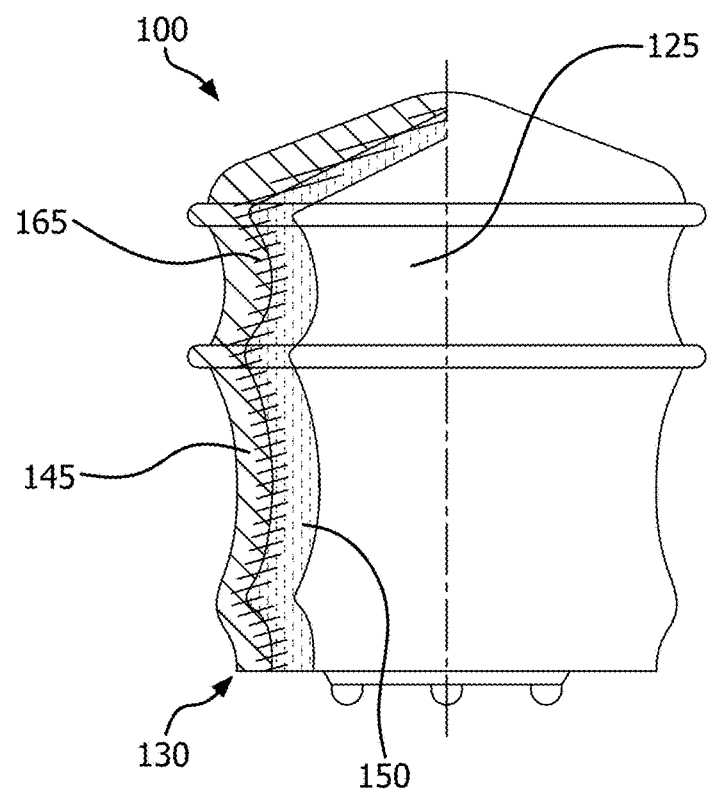

In other embodiments, the material of the barrier layer 145 may at least partially penetrate the porous layer 150. FIG. 6 illustrates a cross-section of a stopper 100 depicting the barrier layer 145, the porous layer 150, and the elastomeric body 125. Specifically, FIG. 6 shows a region of partial penetration 165 of the material of the barrier layer 145 into the porous layer 150. Penetration of the material of the barrier layer 145 into the porous layer 150 improves the bond between the barrier layer 145 and the porous layer 150. The region of partial penetration 165 may also provide support for the barrier layer 145 to impart strength, toughness, compliance and stability, which may be beneficial in both the forming process and in the application.

In some embodiments, the barrier layer 145 may substantially fill the porous layer 150. In another aspect, the porous layer 150 may be filled to a substantially similar degree with barrier layer 145 and elastomer, leaving few open pores in the porous structure. In still another aspect, both the barrier layer 145 and the elastomer partially fill the porous layer 150, while leaving some open pores between them. Other variations of penetration of elastomer and/or the barrier layer 145 may be readily apparent to one of skill in the art. Each may have advantages according to the specific application, with due consideration to the various desirable characteristics of the finished device, such as reduced friction, improved barrier properties, and improved sealing. The degree of penetration of either barrier polymer or elastomer may be controlled by any means known, but include variations in time, temperature, pressure, and porosity of the porous material. In one aspect the porous material may, for example have a porosity that varies with depth.

In yet another embodiment, the barrier layer 145 may be formed of a composite fluoropolymer or non-fluoropolymer material having a barrier layer and a tie layer such as is described in U.S. Patent Publication No. 2016/0022918 to Gunzel. It is to be noted that, as used herein, the term "tie layer" may include fluoropolymer and/or non-fluoropolymer materials. The tie layer can include, or be formed of, expanded polytetrafluoroethylene or other porous expanded fluoropolymers (for example, an ePTFE as taught in U.S. Pat. No. 6,541,589 to Baille). Alternatively, the tie layer may be formed of, or include, non-fluoropolymer materials. Non-limiting examples of suitable non-fluoropolymer materials for use in or as the tie layer include non-fluoropolymer membranes, non-fluoropolymer microporous membranes, non-woven materials (e.g., spunbonded, melt blown fibrous materials, electrospun nanofibers), polyvinylidene difluoride (PVDF), nanofibers, polysulfones, polyethersulfones, polyarlysolfones, polyether ether ketone (PEEK), polyethylenes, polypropylenes, and polyimides.

In a further embodiment, the barrier layer 145 can be made by forming a thin densified composite comprising a porous ePTFE layer and a thermoplastic barrier layer. In this aspect, a thermoplastic having a surface with a low coefficient of friction is preferred. Accordingly, fluoropolymer based thermoplastics such as fluorinated ethylene propylene (FEP), perfluoroalkoxy (PFA), tetrafluororethylene-hexafluoropropylene-vinylidenefluoride (THV) may be applicable. A barrier according to this aspect may be an FEP/ePTFE laminate obtained by following the process taught in WO 94/13469 to Bacino. The barrier may be formed at process temperatures above the softening temperature or even above the melt of the FEP film in a female cavity mold.

In another embodiment, the barrier layer 145 may comprise a composite of a densified ePTFE film and a thin layer of porous ePTFE bonded to the barrier layer film. The densified ePTFE film may be obtained as described in U.S. Pat. No. 7,521,010 to Kennedy et al. The ePTFE/densified ePTFE composite may be combined in the manner described in U.S. Pat. No. 6,030,694 to Dolan, et al. In this embodiment, the composite material comprises a layer of densified ePTFE film and a porous ePTFE layer.

Figure 7:
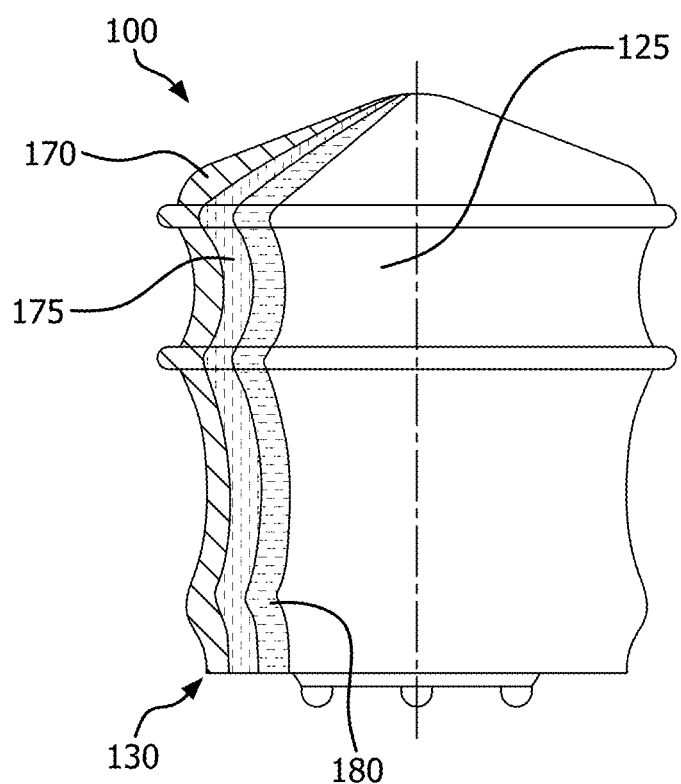
Figure 8:
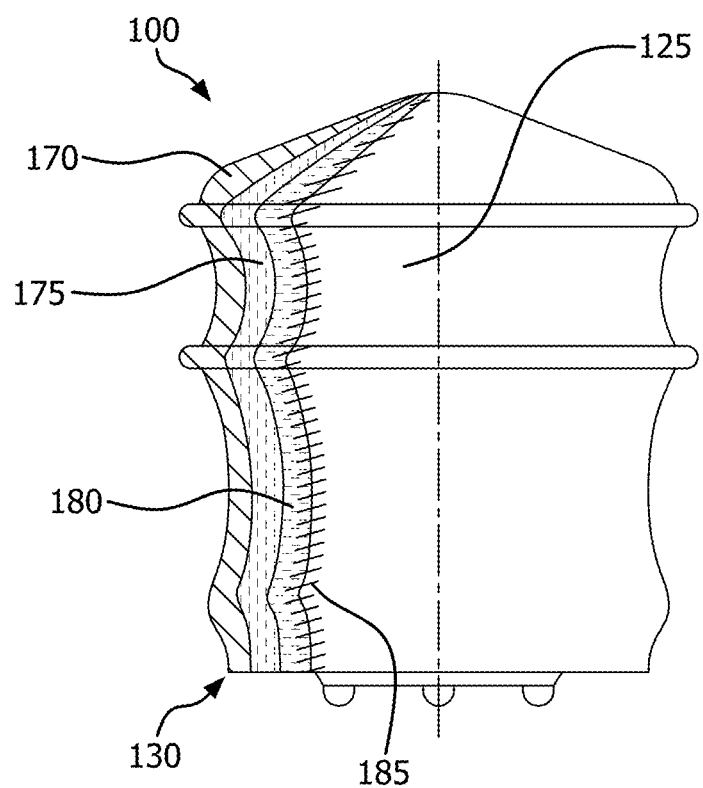
Figure 9:
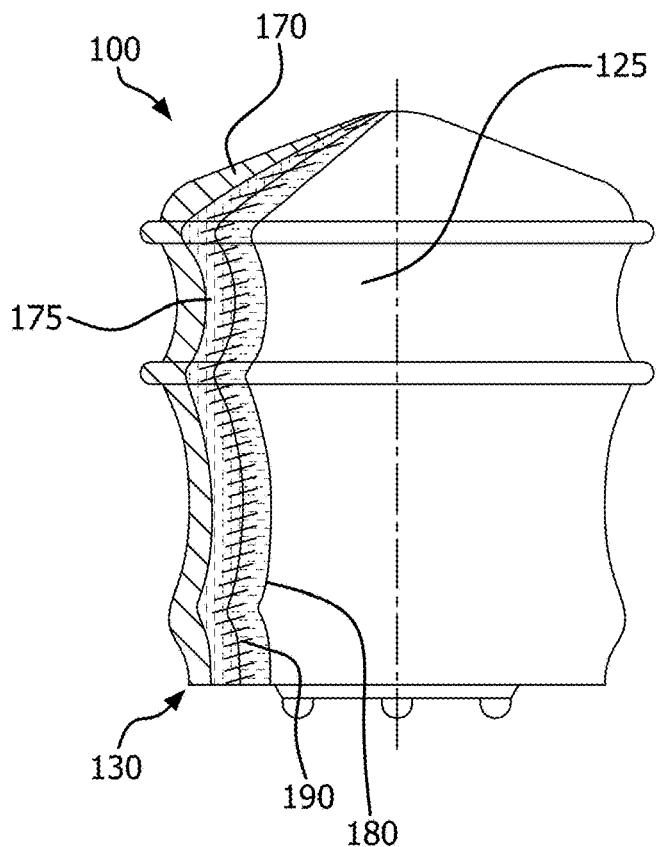
Figure 10:
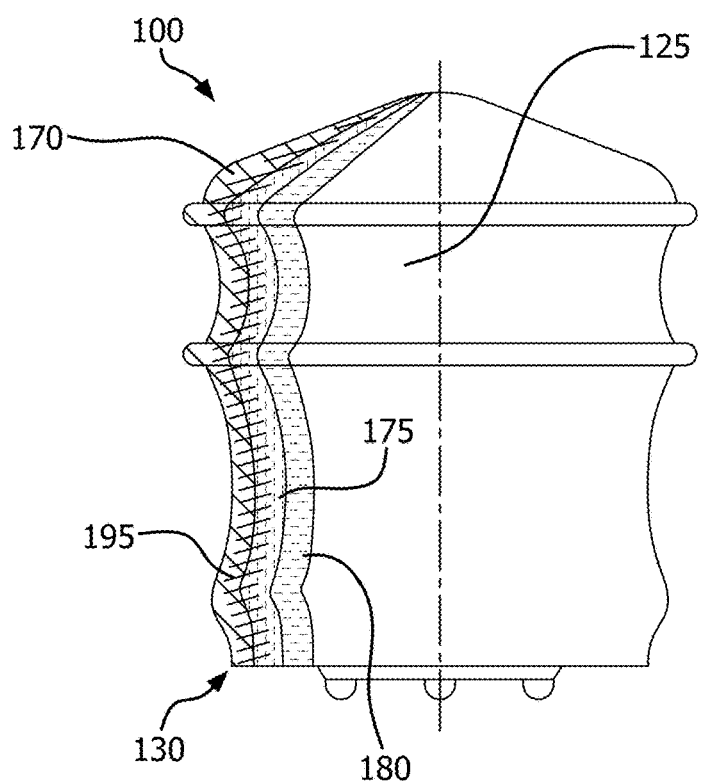

In another embodiment, as shown in FIG. 7, the laminate layer 130 includes a composite material having at least three layers, namely, a densified expanded fluoropolymer layer 170, a barrier melt fluoropolymer layer 175, and a porous layer 180. The densified expanded fluoropolymer layer 170 may include or be formed of a densified ePTFE. The barrier melt fluoropolymer layer 175 may include a fluoropolymer such as a densified expanded fluoropolymer, polytetrafluoroethylene (PTFE), expanded polytetrafluorethylene (ePTFE), densified expanded polytetrafluoroethylene, fluorinated ethylene propylene (FEP), polyvinylidene fluoride, polyvinylfluoride, perfluoropropylvinylether, perfluoroalkoxy polymers, and copolymers and combinations thereof. Non-limiting examples of non-fluoropolymers that may be utilized in the barrier melt layer 175 include polyethylene and polypropylene. The porous layer 180 may include or be formed of ePTFE or other porous expanded fluoropolymers. The laminate layers 130 having the densified expanded fluoropolymer layer 170, the barrier melt fluoropolymer layer 175 and the porous layer 180 may be constructed by coating or otherwise depositing the densified expanded fluoropolymer onto the porous layer to create the composite material. In one non-limiting embodiment, the laminate layer 130 is formed of a densified fluoropolymer (e.g., densified ePTFE), a thermoplastic adhesive (e.g., FEP), and a porous fluoropolymer (e.g., ePTFE). In accordance with some aspects, the elastomer material of the elastomeric body 125 may at least partially penetrate the porous layer 180 as shown by reference numeral 185 in FIG. 8. In accordance with other embodiments, the material of the barrier melt fluoropolymer layer 175 may at least partially penetrate the porous layer 180 as shown by reference numeral 190 in FIG. 9. In other embodiments, the material of the barrier melt fluoropolymer layer 175 may at least partially penetrate the densified expanded fluoropolymer layer 170, such as is shown by reference numeral 195 depicted in FIG. 10.

It is to be appreciated that the stopper 100 may include various degrees of penetration of either the elastomer material or the barrier polymer into the porous material or the densified expanded fluoropolymer layer as depicted herein and as described in U.S. Pat. No. 8,722,178 to Ashmead, et al., U.S. Pat. No. 9,597,458 to Ashmead, et al., and U.S. Patent Publication No. 2016/0022918 to Gunzel. It is also to be appreciated that there are many variations of the processes described herein that could be utilized for forming the stopper 100 without departing from the scope and/or spirit the invention.

The barrels 20, 401 may be formed of a substantially rigid or hard material, such as a glass material (e.g., borosilicate glass), a ceramic material, one or more polymeric materials (e.g., polypropylene, polyethylene, and copolymers thereof), a metallic material, or a plastic material (e.g., cyclic olefin polymers (COC) and cyclic olefin copolymers (COP), and combinations thereof. It is to be appreciated that barrels formed of materials that are not inherently hydrophobic (e.g. a glass barrel) may be coated or otherwise treated so as to be rendered hydrophobic. In exemplary embodiments, the barrels 20, 401 have a hydrophobic interior wall characterized by the absence of a lubricant such as, but not limited to, silicone or silicone oil. As used herein, the term "hydrophobic interior wall" refers to the interior surface of a barrel that is free or substantially free (i.e., has an unquantifiable or trace amount) of silicone oil. In addition, the hydrophobic surfaces of the barrels 20, 401 also have a contact angle of deionized water on a flat surface of the material greater than 90°, indicating a hydrophobic surface. In some embodiments, the water contact angle is from about 90° to about 180° or from about 96° to about 180°, from about 96° to about 130, or from about 96° to about 120°.

Figure 11A:
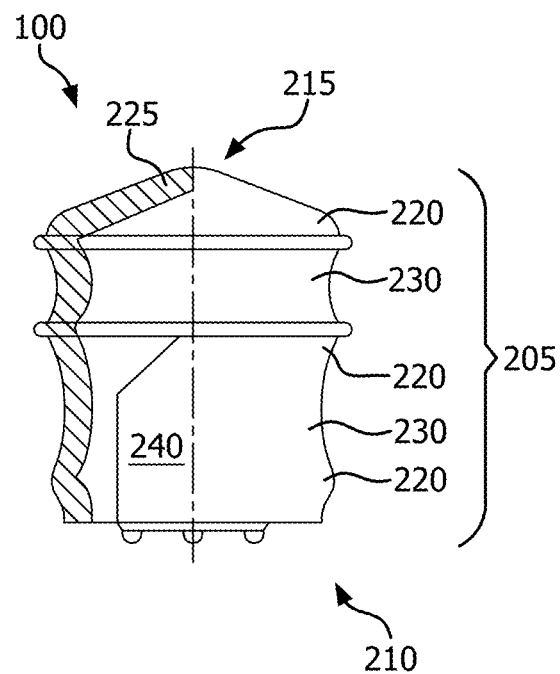
FIGS. 11A and 11B are schematic illustrations of stoppers in accordance with some embodiments.
Figure 11B:
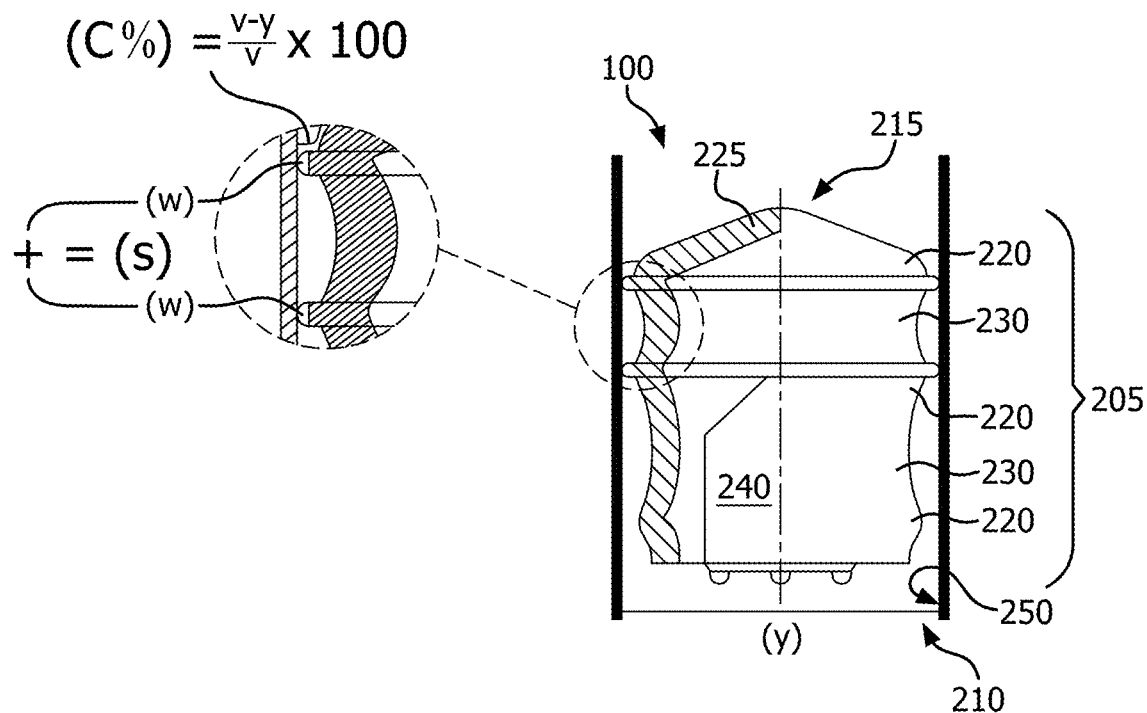

The stopper 100 may be configured to achieve container closure integrity with high levels of air and liquid impermeability while also maintaining one or more of: acceptably low break loose force, low average glide force, and low glide force variation. FIGS. 11A and 11B depict a stopper 100 that includes a body 205 having opposed proximal and distal ends 210 and 215 and two or more ribs 220. A head portion 225 is formed integrally with the distal end 215 of the body 205. One or more annular grooves 230 is formed in an outer surface of the body 205, thus forming and connecting the two or more ribs 220. At least one of the two or more ribs 220 is laminated with the laminate layers 130. A cavity 240 may extend from the proximal end of 210 of the body 205 towards the distal end 215.

As the skilled artisan will appreciate, the ribs 220 can be structured in any number of configurations, and FIGS. 11A and 11B are provided for purposes of illustration only, and are not intended to limit the present disclosure. For example, only the distal or leading rib may have a sealing surface. As used herein, the term "sealing surface" is meant to define a rib that effectively maintains a liquid-tight seal with the inner surface of the barrel both in storage and in use. It is to be appreciated that the quality of a seal thus formed may be assessed by any number of methods familiar to one skilled in the art (e.g. helium leak). In some embodiments, multiple ribs may have a sealing surface. In one or more embodiment, all of the ribs 220 having a sealing surface may have a same predefined outer diameter (x). In other embodiments, each rib 220 having a sealing surface may have its own predefined outer diameter (x). For example, a distal or leading rib may have a predefined outer diameter (x) and a proximal or trailing rib may have a predefined outer diameter (y) that is between about 75% and about 99.9% of the predefined outer diameter (x). Other types of rib arrangements are contemplated, such as, for example having three ribs with sealing surfaces, without departing from the spirit and scope of the present disclosure Additionally, each rib 220 having a sealing surface includes at least one predefined outer diameter (x) measured from an apex of the respective rib with the stopper 100 in a non-compressed state (see, e.g., FIG. 11A) and a contact width (w) between each respective rib and an inner surface 250 of the barrel measured at a compressibility (C %) of the stopper 100 in a compressed state (see, e.g., FIG. 11B).

In some embodiments, the stopper 100 may be configured based on the aforementioned composition of the laminate layers 130 and properties of the two or more ribs 220 to have a predetermined break loose force and predetermined seal pressure. In the embodiments described below, the predetermined break loose force is a peak extrusion force of less than about 20 N at speeds of 50-250 mm/min using a syringe filled with water when tested according to the Break Loose Force test method described herein. Also, the predetermined seal pressure is a seal pressure adequate to achieve a helium leak rate of less than $6\times10^{-6}$ sccs. In addition, the compressibility of the stopper is greater than about 4.5%.

Embodiment Number 1

In a first embodiment, a stopper as described above is utilized in a medical delivery device (e.g., a syringe, auto-injector, or a pen) and has a compressibility percentage (C %) that is less than about 7.9%. For instance, the stopper may have a compressibility percentage that is between about 4.5% and about 7.9%, between about 5.0% and about 7.9%, between about 5.5% and about 7.9%, between about 6.0% and about 7.9%, or between about 6.5% and about 7.9%. Compressibility (C %) is defined in relation to a maximum outer diameter (v) of the ribs 220 having a sealing surface of the stopper 100 in a non-compressed state and the inner diameter (y) of the inner surface 250 of the barrel as follows: C %=((v−y)/v)×100. For example, understanding that each of the ribs 220 having a sealing surface may have its own predefined outer diameter (x), and thus its own compression, compressibility (C %) of the stopper 100 is defined in relation to the largest outer diameter (x) (i.e., the maximum outer diameter (v)) out of all of the ribs 220 having a sealing surface of the stopper 100 in a non-compressed state.

In addition, the stopper 100 includes a sliding surface (S), which is a sum of the contact widths (w) of all the ribs having a sealing surface. The sliding surface is less than about 2.0 mm. In some embodiments, the sliding surface may be between about 0.3 mm and about 2.0 mm, between about 0.62 mm and about 1.5 mm, or between about 0.85 and about 1.3 mm.

Referring to FIGS. 11A and 11B, the seal pressure of a stopper laminated with a fluoropolymer film that is in contact with a hydrophobic or lubricant free inner surface of a barrel depends particularly upon compressibility (C %), and the break loose force (e.g., the amount of force required to begin moving the stopper from a stationary position within the barrel) and average glide force (e.g., the amount of force required to move the stopper parallel along the inner surface of the barrel) particularly depend upon the contact width (w) or sliding surface (S).

The average glide force of the stopper in the barrel is less than about 4.0 N. As used herein, the term "average glide force" is meant to describe the average glide force recorded between 10 mm and 28 mm for a 1 ml long syringe when tested according to the Average Glide Force test method described herein. The average glide force may be less than about 3.5 N, less than about 3 N, less than about 2.5 N, less than about 2 N, less than about 1.5 N, or less than about 1 N. Alternatively, the average glide force may be from about 1 N to about 4.0 N, from about 1.5 N to about 3.5 N, from about 2 N to about 3.5 N, or from about 2 N to about 3 N. Additionally, the stopper may have a glide force variation less than about 1.3 N when calculated according to the Glide Force Variation test method described herein. In some embodiments, the stopper may have a glide force variation from about 0.01 N to about 1.3 N, from about 0.01 N to about 0.9 N, from about 0.01 N to about 0.8 N, from about 0.01 N to about 0.7 N, from about 0.01 N to about 0.6 N, from about 0.01 N to about 0.5 N, from about 0.01 N to about 0.4 N, from about 0.01 N to about 0.3 N, from about 0.01 N to about 0.25 N, from about 0.01 N to about 0.2 N, or from about 0.01 N to about 0.1 N when calculated according to the Glide Force Variation test method described herein. In some embodiments, the break loose force may be less than about 7.0 N.

It has been surprisingly and unexpectedly found that when the compressibility of the sealing ribs is between about 4.5% and about 7.9% and the sliding surface (S) of the stopper 100 is less than about 2.0 mm, the stoppers achieve adequate seal with a low break loose force, low average glide force, and low glide force variation.

Embodiment Number 2

In a second embodiment, a stopper as described above is utilized in a medical delivery device (e.g., a syringe, auto-injector, or a pen) and has a compressibility percentage (C %) that is between about 4.5% and about 7.9%. For instance, the stopper may have a compressibility percentage that is between about 4.5% and about 7.9%, between about 5.0% and about 7.9%, between about 5.5% and about 7.9%, between about 6.0% and about 7.9%, or between about 6.5% and about 7.9%. The stopper 100 also includes a sliding surface (S) that is greater than about 2.0 mm. In some embodiments, the sliding surface may be between about 2.0 mm and about 3.2 mm, between about 2.0 mm and about 3.0 mm or between about 2.0 mm and about 2.5 mm.

The average glide force of the stopper in the barrel is less than about 7.0 N. In some embodiments, the average glide force may be less than about 6.0 N, less than about 5.0 N, less than about 4.0 N, or less than about 3.0 N. Alternatively, the average glide force may be from about 3.0 N to about 7.0 N, from about 3.0 N to about 6.0 N, from about 3.0 N to about 5.0 N, or from about 3.0 N to about 4.0 N. Additionally, the stopper may have a glide force variation less than about 1.3 N when calculated according to the Glide Force Variation test method described herein. In some embodiments, the stopper may have a glide force variation from about 0.01 N to about 1.3 N, from about 0.01 N to about 0.9 N, from about 0.01 N to about 0.8 N, from about 0.01 N to about 0.7 N, from about 0.01 N to about 0.6 N, from about 0.01 N to about 0.5 N, from about 0.01 N to about 0.4 N, from about 0.01 N to about 0.3 N, from about 0.01 N to about 0.25 N, from about 0.01 N to about 0.2 N, or from about 0.01 N to about 0.1 N when calculated according to the Glide Force Variation test method described herein. In some embodiments, the break loose force may be between about 4.0 N and 10.0 N.

It has been surprisingly and unexpectedly found that when the compressibility of the sealing ribs is between about 4.5% and about 7.9% and the sliding surface (S) of the stopper 100 is greater than about 2.0 mm but less than about 3.2 mm, the stoppers achieve adequate seal with an acceptable break loose force, acceptable glide force and low glide force variation.

Embodiment Number 3

In a third embodiment, a stopper as described above is utilized in a medical delivery device (e.g., a syringe, auto-injector, or a pen) and has a compressibility percentage (C %) that is greater than about 7.9%. For example, the stopper may have a compressibility percentage that is between about 7.9% and about 17.0%, between about 7.9% and about 13%, between about 7.9% and about 11%, between about 7.9% and about 10.0%, or between about 7.9% and about 9.0%. The stopper 100 also includes a sliding surface (S) that is greater than about 2.0 mm. In some embodiments, the sliding surface may be between about 2.0 mm and about 3.2 mm, between about 2.0 mm and about 2.8 mm, or between about 2.0 mm and about 2.5 mm.

Additionally, the stopper may have a glide force variation less than about 1.3 N when calculated according to the Glide Force Variation test method described herein. In some embodiments, the stopper may have a glide force variation from about 0.01 N to about 1.3 N, from about 0.01 N to about 0.9 N, from about 0.01 N to about 0.8 N, from about 0.01 N to about 0.7 N, from about 0.01 N to about 0.6 N, from about 0.01 N to about 0.5 N, from about 0.01 N to about 0.4 N, from about 0.01 N to about 0.3 N, from about 0.01 N to about 0.25 N, from about 0.01 N to about 0.2 N, or from about 0.01 N to about 0.1 N when calculated according to the Glide Force Variation test method described herein. The break loose force may be between about 6.0 N and about 20.0 N.

It has been surprisingly and unexpectedly found that when the compressibility of the sealing ribs is between about 7.9% and about 17.0% and the sliding surface (S) of the stopper 100 is greater than about 2.0 mm but less than about 3.2 mm, the stoppers achieve adequate seal with an acceptable break loose force, acceptable glide force and low glide force variation.

Embodiment Number 4

In a fourth embodiment, a stopper as described above is utilized in a medical delivery device (e.g., a syringe, auto-injector, or a pen) and has a compressibility percentage (C %) that is greater than about 7.9%. For example, the stopper may have a compressibility percentage that is between about 7.9% and about 17%, between about 7.9% and about 13%, between about 7.9% and about 11%, or between about 7.9% and about 9.0%. The stopper 100 also includes a sliding surface (S) that is less than about 2.0 mm. In some embodiments, the sliding surface may be between about 0.3 mm and about 2.0 mm, between about 0.7 mm and about 1.5 mm, or between about 0.7 mm and about 1.1 mm.

The average glide force of the stopper in the barrel is less than about 9.0 N. The average glide force may be less than about 7.0 N, or less than about 6.0 N. Alternatively, the average glide force may be from about 2.0 N to about 9.0 N, from about 3.0 N to about 8.0 N, from about 3.0 N to about 7.0 N, or from about 3.0 N to about 6.0 N. Additionally, the stopper may have a glide force variation less than about 0.2 N when calculated according to the Glide Force Variation test method described herein. In some embodiments, the stopper may have a glide force variation from about 0.01 N to about 0.15 N or from about 0.01 N to about 0.1 N when calculated according to the Glide Force Variation test method described herein. The break loose force may be between about 2.0 N and about 13 N.

It has been surprisingly and unexpectedly found that when the compressibility of the sealing ribs is between about 7.9% and about 17% and the sliding surface (S) of the stopper 100 is less than about 2.0 mm, the stoppers achieve adequate seal with low glide force variation.

The medical delivery devices and stoppers described herein may be used in combination different therapeutic compounds such as, for example, drugs and biologics, including but not limited to, antibodies, antisense, RNA interference, gene therapy, primary and embryonic stem cells, vaccines, and combinations thereof. For instance, the embodiments described herein may be utilized in combination with any or all of the following:

Cell therapy using cells that are derived primarily from endoderm such as Exocrine secretory epithelial cells and Hormone-secreting cells; ectoderm such as Keratinizing epithelial cells, Wet stratified barrier epithelial cells, Sensory transducer cells, Autonomic neuron cells, Sense organ and peripheral neuron supporting cells, Central nervous system neurons and glial cells, Lens cells; mesoderm such as Metabolism and storage cells, Barrier function cells (lung, gut, exocrine glands, and urogenital tract), Extracellular matrix cells, Contractile cells, Blood and immune system cells, Germ cells, Nurse cell, Interstitial cells or a combination thereof. Additionally cells that are genetically, chemically or physically altered or modified are considered to be in the scope of the invention.

Examples of Exocrine secretory epithelial cells include, but are not limited to, Salivary gland mucous cell, Salivary gland number 1, Von Ebner's gland cell in tongue, Mammary gland cell, Lacrimal gland cell, Ceruminous gland cell in ear, Eccrine sweat gland dark cell, Eccrine sweat gland clear cell, Apocrine sweat gland cell, Gland of Moll cell in eyelid, Sebaceous gland cell, Bowman's gland cell in nose, Brunner's gland cell in duodenum, Seminal vesicle cell, Prostate gland cell, Bulbourethral gland cell, Bartholin's gland cell, Gland of Littre cell, Uterus endometrium cell, Isolated goblet cell of respiratory and digestive tracts, Stomach lining mucous cell, Gastric gland zymogenic cell, Gastric gland oxyntic cell, Pancreatic acinar cell, Paneth cell of small intestine, Type II pneumocyte of lung, Clara cell of lung; Hormone-secreting cells including but not limited to: Anterior pituitary cells, Intermediate pituitary cell, Magnocellular neurosecretory cells, Gut and respiratory tract cells, Thyroid gland cells, Parathyroid gland cells, Adrenal gland cells, Leydig cell of testes secreting testosterone, Theca interna cell of ovarian follicle secreting estrogen, Corpus luteum cell of ruptured ovarian follicle secreting progesterone, Juxtaglomerular cell, Macula densa cell of kidney, Peripolar cell of kidney, Mesangial cell of kidney, Pancreatic islets; Keratinizing epithelial cells including but not limited to: Epidermal keratinocyte, Epidermal basal cell, Keratinocyte of fingernails and toenails, Nail bed basal cell, Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell; Wet stratified barrier epithelial cells including but not limited to: Surface epithelial cell of stratified squamous epithelium and basal cell of epithelia of cornea, tongue, oral cavity, esophagus, anal canal, distal urethra and vagina, Urinary epithelium cell; Sensory transducer cells including but not limited to: Auditory inner hair cell of organ of Corti, Auditory outer hair cell of organ of Corti, Basal cell of olfactory epithelium, Cold-sensitive primary sensory neurons, Heat-sensitive primary sensory neurons, Merkel cell of epidermis, Olfactory receptor neuron, Pain-sensitive primary sensory neurons, Photoreceptor cells of retina in eye: Proprioceptive primary sensory neurons, Touch-sensitive primary sensory neurons, Type I carotid body cell, Type II carotid body cell, Type I hair cell of vestibular system of ear, Type II hair cell of vestibular system of ear, Type I taste bud cell; Autonomic neuron cells including but not limited to: Cholinergic neural cell, Adrenergic neural cell, Peptidergic neural cell; Sense organ and peripheral neuron supporting cells including but not limited to: Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Taste bud supporting cell, Olfactory epithelium supporting cell, Schwann cell, Satellite glial cell, Enteric glial cell; Central nervous system neurons and glial cells including but not limited to: Astrocyte, Neuron cells, Oligodendrocyte, Spindle neuron; Lens cells including but not limited to: Anterior lens epithelial cell, Crystallin-containing lens fiber cell; Metabolism and storage cells including but not limited to: Adipocytes: Liver lipocyte; Barrier function cells including but not limited to: Kidney parietal cell, Kidney glomerulus podocyte, Kidney proximal tubule brush border cell, Loop of Henle thin segment cell, Kidney distal tubule cell, Kidney collecting duct cell, Principal cells, Intercalated cells, Type I pneumocyte, Pancreatic duct cell, Nonstriated duct cell, Principal cell, Intercalated cell, Duct cell, Intestinal brush border cell, Exocrine gland striated duct cell, Gall bladder epithelial cell, Ductulus efferens nonciliated cell, Epididymal principal cell, Epididymal basal cell; Extracellular matrix cells including but not limited to: Ameloblast epithelial cell, Planum semilunatum epithelial cell of vestibular system of ear, Organ of Corti interdental epithelial cell, Loose connective tissue fibroblasts, Corneal fibroblasts, Tendon fibroblasts, Bone marrow reticular tissue fibroblasts, Other nonepithelial fibroblasts, Pericyte, Nucleus pulposus cell of intervertebral disc, Cementoblast/cementocyte, Odontoblast/odontocyte, Hyaline cartilage chondrocyte, Fibrocartilage chondrocyte, Elastic cartilage chondrocyte, Osteoblast/osteocyte, Osteoprogenitor cell, Hyalocyte of vitreous body of eye, Stellate cell of perilymphatic space of ear, Hepatic stellate cell, Pancreatic stelle cell; Contractile cells including but not limited to: Skeletal muscle cell, Satellite cell, Heart muscle cells, Smooth muscle cell, Myoepithelial cell of iris, Myoepithelial cell of exocrine glands; Blood and immune system cells including but not limited to: Erythrocyte, Megakaryocyte, Monocyte, Connective tissue macrophage, Epidermal Langerhans cell, Osteoclast, Dendritic cell, Microglial cell, Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells and committed progenitors for the blood and immune system; Germ cells including but not limited to: Oogonium/Oocyte, Spermatid, Spermatocyte, Spermatogonium cell, Spermatozoon; Nurse cell including but not limited to: Ovarian follicle cell, Sertoli cell, Thymus epithelial cell; Interstitial cells including but not limited to: Interstitial kidney cells and a combination thereof.

Examples of antibodies, antisense, RNA interference, or gene therapy made to protein targets or gene(s) of: Ataxia Telangiectasia Mutated, Tumor Protein p53, Checkpoint kinase 2, breast cancer susceptibility protein, Double-strand break repair protein, DNA repair protein RAD50, Nibrin, p53-binding protein, Mediator of DNA damage checkpoint protein, H2A histone family member X, Microcephalin, C-term inal-binding protein 1, Structural maintenance of chromosomes protein 1A; Esterases; Phosphatases; Examples of Ion channels include but are not limited to: ligand-gated ion channels, voltage-gated ion channels; Examples of growth factors include but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-β), b, one morphogenetic proteins (BMPs), Activin, inhibin, fibroblast growth factors (FGFs), granulocyte-colony stimulating factor (G-CSF), granulocyte-macrophage colony stimulating factor (GM-CSF), glial cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HDGF), Insulin-like growth factors; Examples of G Protein-Coupled Receptors (GPCR) include but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin A receptor (CCK1), Cholecystokinin B receptor (CCK2), Chemokine (C—C motif) receptor family, Sphingosine 1-phosphate receptor family, Succinic receptor, Cholinergic receptor family. Chemokine-like receptor family, Cannabinoid receptor family, Corticotropin releasing hormone receptor family, prostaglandin D2 receptor, Chemokine C—X3-C receptor family, Chemokine (C—X—C motif) receptor family, Burkitt lymphoma receptor, Chemokine (C—X—C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G-protein coupled receptor (C5L2, FFA4, FFA4, FFA4, GPER, GPR1, GPR101, GPR107, GPR119, GPR12, GPR123, GPR132, GPR135, GPR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonadotropin receptor (LH), Leukotriene B4 receptor (BLT1), Adenylate Cyclase Activating Polypeptide 1 Receptor 1 (mPAC1), Motilin receptor, Melanocortin receptor family, Melanin concentrating hormone receptor 1 (MCH1), Neuropeptide Y1 receptor (Y1), Neuropeptide Y2 receptor (NPY2R), Opioid receptor family, Oxytocin recepter (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides B/W receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPN5), Opioid receptor-like receptor (NOP), Oxoeicosanoid (OXE) receptor 1 (OXE), Oxoglutarate (alpha-ketoglutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin 12 (prostacyclin) receptor family, Parathyroid hormone receptor family, muscarinic 4 (rM4), Prostanoid DP2 receptor (rGPR44), Prokineticin receptor family, Relaxin family peptide receptor family, Secretin receptor (secretin), Smoothened, Frizzled class receptor (Smoothened), trace amine associated receptor family, Tachykinin family, Thromboxane A2 receptor (TP), Thyrotropin-releasing hormone receptor (TRH1), Thyroid Stimulating Hormone Receptor (TSH); Examples of Protein kinases include but are not limited to: AP2 associated kinase, Homo sapiens ABL proto-oncogene 1—non-receptor tyrosine-protein kinase family, c-abl oncogene 1 receptor tyrosine kinase family, v-abl Abelson murine leukemia viral oncogene homolog 2, activin A receptor family, chaperone—ABC1 activity of bc1 complex homolog (S. pombe) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family—SNF1-like kinase, mitogen-activated protein kinase kinase kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLK), bone morphogenetic protein receptor family, BMX non-receptor tyrosine kinase (BMX), v-raf murine sarcoma viral oncogene homolog B1 (BRAF), protein tyrosine kinase 6 (BRK), BR serine/threonine kinase family, Bruton agammaglobulinemia tyrosine kinase (BTK), calcium/calmodulin-dependent protein kinase family, cyclin-dependent kinase family, cyclin-dependent kinase-like family, CHK1 checkpoint homolog (S. pombe) (CHEK1), CHK2 checkpoint homolog (S. pombe) (CHEK2), Insulin receptor, isoform A (INSR), Insulin receptor, isoform B (INSR), rho-interacting serine/threonine kinase (CIT), v-kit Hardy-Zuckerman 4 feline sarcoma viral oncogene homolog (KIT), CDC-Like Kinase family—Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fps/fes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family, fyn-related kinase (FRK), FYN oncogene related to SRC, cyclin G associated kinase (GAK), eukaryotic translation initiation factor 2 alpha kinase, Growth hormone receptor. G protein-coupled receptor kinase 1 (GRK1), G protein-coupled receptor kinase family, glycogen synthase kinase family, germ cell associated 2 (haspin) (HASPIN), Hemopoietic cell kinase (HCK), homeodomain interacting protein kinase family, mitogen-activated protein kinase kinase kinase kinase family, hormonally up-regulated Neu-associated kinase (HUNK), intestinal cell (MAK-like) kinase (ICK), Insulin-like growth factor 1 receptor (IGF1 R), conserved helix-loop-helix ubiquitous kinase (IKK-alpha), inhibitor of kappa light polypeptide gene enhancer in B-cells—kinase beta family, insulin receptor (INSR), insulin receptor-related receptor (INSRR), interleukin-1 receptor-associated kinase family, IL2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serine/threonine kinase family leucine-rich repeat kinase family, v-yes-1 Yamaguchi sarcoma viral related oncogene homolog (LYN), male germ cell-associated kinase (MAK), MAP/microtubule affinity-regulating kinase family, microtubule associated serine/threonine kinase family, maternal embryonic leucine zipper kinase, c-mer proto-oncogene tyrosine kinase (MERTK), met proto-oncogene (hepatocyte growth factor receptor), MAP kinase interacting serine/threonine kinase family, myosin light chain kinase family, mixed lineage kinase domain-like protein isoform, CDC42 binding protein kinase family, serine/threonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serine/threonine-protein kinase NIM1 (NIM1), nemo-like kinase (NLK), oxidative-stress responsive 1 (OSR1), p21 protein (Cdc42/Rac)-activated kinase family, PAS domain containing serine/threonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4,5-bisphosphate 3-kinase, phosphoinositide-3-kinase family, phosphatidylinositol 4-kinase family. phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosine/threonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serine/threonine and tyrosine protein kinase (RIPK5), Rho-associated, coiled-coil containing protein kinase family, c-ros oncogene 1, receptor tyrosine kinase (ROS1), ribosomal protein S6 kinase family, SH3-binding domain kinase 1 (SBK1), serum/glucocorticoid regulated kinase family, Putative uncharacterized serine/threonine-protein kinase (Sugen kinase 110) (SgK110), salt-inducible kinase family, SNF related kinase (SNRK), src-related kinase, SFRS protein kinase family, Spleen tyrosine kinase (SYK), TAO kinase family, TANK-binding kinase 1 (TBK1), tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting kinase (TNIK), non-receptor tyrosine kinase family, TNNI3 interacting kinase (TNNI3K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, WNK lysine deficient protein kinase family, v-yes-1 Yamaguchi sarcoma viral oncogene homolog 1 (YES), sterile alpha motif and leucine zipper containing kinase AZK (ZAK), zeta-chain (TCR) associated protein kinase 70 kDa (ZAP70); Examples of nuclear hormone receptors include but are not limited to: Androgen receptor (AR), Estrogen related receptor alpha (ESRRA), Estrogen receptor 1 (ESR1), Nuclear receptor subfamily 1—group H—member 4 (NR1H4), Nuclear receptor subfamily 3—group C—member 1 (glucocorticoid receptor) (NR3C1), Nuclear receptor subfamily 1—group H—member 3 (Liver X receptor α) (NR1H3), Nuclear receptor subfamily 1—group H—member 2 (Liver X receptor β) (NR1 H2), Nuclear receptor subfamily 1—group H—member 2 (Liver X receptor β) (NR1 H2), Nuclear receptor subfamily 3—group C—member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor a (PGR), Progesterone receptor β (PGR), Retinoic acid receptor—alpha (RARA), Retinoic acid receptor—beta (RARB), Retinoid X receptor—alpha (RXRA), Retinoid X receptor—gamma (RXRG), Thyroid hormone receptor—alpha (THRA), Thyroid hormone receptor—beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, Nerve growth factor-induced-B, Germ cell nuclear factor; Examples of Epigenetic targets include but are not limited to: ATPase family AAA domain-containing protein 2 (ATAD2A), ATPase family—AAA domain containing 2B (ATAD2B), ATPase family AAA domain containing—2B (ATAD2B), bromodomain adjacent to zinc finger domain—1A (BAZ1A), bromodomain adjacent to zinc finger domain—1B (BAZ1B), bromodomain adjacent to zinc finger domain—2A (BAZ2A), bromodomain adjacent to zinc finger domain—2A (BAZ2A), bromodomain adjacent to zinc finger domain—2B (BAZ2B), bromodomain-containing protein 1 (BRD1), Bromodomain containing protein 2—1st bromodomain (BRD2), Bromodomain containing protein 2—1st & 2nd bromodomains (BRD2), bromodomain-containing protein 2 isoform 1—bromodomain 2 (BRD2(2)), bromodomain-containing protein 3—bromodomain 1 (BRD3(1)), Bromodomain-containing protein 3—1st bromodomain (BRD3), Bromodomain-containing protein 3—1st & 2nd bromodomains (BRD3), bromodomain-containing protein 3—bromodomain 2 (BRD3(2)), Bromodomain containing protein 4—1st bromodomain (BRD4), bromodomain-containing protein 4 isoform long—bromodomains 1 and 2 (BRD4(1 -2)), bromodomain-containing protein 4 isoform long—bromodomain 2 (BRD4(2)), bromodomain-containing protein 4 isoform short (BRD4(full-length-short-iso.)), Bromodomain containing protein 7 (BRD7), bromodomain containing 8—bromodomain 1 (BRD8(1)), bromodomain containing 8—bromodomain 2 (BRD8(2)), bromodomain-containing protein 9 isoform 1 (BRD9), Bromodomain containing testis-specific—1st bromodomain (BRDT), Bromodomain containing testis-specific—1st & 2nd bromodomains (BRDT), bromodomain testis-specific protein isoform b—bromodomain 2 (BRDT(2)), bromodomain and PHD finger containing—1 (BRPF1), bromodomain and PHD finger containing—3 (BRPF3), bromodomain and PHD finger containing—3 (BRPF3), Bromodomain and WD repeat-containing 3—2nd bromodomain (BRWD3(2)), Cat eye syndrome critical region protein 2 (CECR2), CREB binding protein (CREBBP), E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase—KAT2A (GCN5L2), Euchromatic histone-lysine N-methyltransferase 1 (EHMT1), Histone-lysine N-methyltransferase MLL (MLL), Polybromo 1—1st bromodomain (PB1(1)), Polybromo 1-2nd bromodomain (PB1(2)), polybromo 1—bromodomain 2 (PBRM1(2)), polybromo 1—bromodomain 5 (PBRM1(5)), Histone acetyltransferase KAT2B (PCAF), PH-interacting protein—1st bromodomain (PHIP(1)), PH-interacting protein—2nd bromodomain (PHIP(2)), Protein kinase C-binding protein 1 (PRKCBP1), Protein arginine N-methyltransferase 3 (PRMT3), SWI/SNF related—matrix associated—actin dependent regulator of chromatin—subfamily a—member 2 (SMARCA2), SWI/SNF related—matrix associated—actin dependent regulator of chromatin—subfamily a—member 4 (SMARCA4), Nuclear body protein—SP110 (SP110), Nuclear body protein—SP140 (SP140), Transcription initiation factor TFIID subunit 1 (TAF1(1 -2)), TAF1 RNA polymerase II—TATA box binding protein (TBP)-associated factor—250 kDa—bromodomain 2 (TAF1(2)), Transcription initiation factor TFIID subunit 1-like—1st bromodomain (TAF1L(1)), Transcription initiation factor TFIID subunit 1-like—2nd bromodomain (TAF1L(2)), tripartite motif containing 24 (TRIM24(Bromo.)), tripartite motif containing 24 (TRIM24 (PHD-Bromo.)), E3 ubiquitin-protein ligase TRIM33 (TRIM33), tripartite motif containing 33 (TRIM33(PHD -Bromo.)), WD repeat 9—1st bromodomain (WDR9(1)), WD repeat 9—2nd bromodomain (WDR9(2)); membrane transport proteins including but not limited to ATP-binding cassette (ABC) superfamily, solute carrier (SLC) superfamily, multidrug resistance protein 1 (P-glycoprotein), organic anion transporter 1,and protein such as EAAT3, EAAC1, EAAT1, GLUT1, GLUT2, GLUT9, GLUT10, rBAT, AE1, NBC1, KNBC, CHED2, BTR1, NABC1, CDPD, SGLT1, SGLT2, NIS, CHT1, NET, DAT, GLYT2, CRTR, BOAT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGC1, ARALAR, Citrin, STLN2, aralar2, TPC, MUP1, MCPHA, CACT, GC1, PHC, DTD, CLD, DRA, PDS, Prestin, TAT1, FATP4, ENT3, ZnT2, ZnT10, AT1, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATP1B1, OATP1B3, OATP2A1; structural proteins including but not limited to tubulin, heat shock protein, Microtubule-stabilizing proteins, Oncoprotein 18, stathmin, kinesin-8 and kinesin-14 family, Kip3, Kif18A; proteases including but not limited ADAM (a disintegrin and metalloprotease) family; Other molecule targets in signal transductions include but are not limited to: Cell division cycle 25 homolog A (CDC25A), forkhead box O3 (forkhead box O3), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1), Tumor necrosis factor receptor superfamily, member 11a (TNFRSF11A), v-rel reticuloendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), Catenin (cadherin-associated protein), beta 1 (CTNNB1), and combinations thereof.

Examples of known biologics include, but are not limited to: Abbosynagis, Abegrin, Actemra, AFP-Cide, Antova, Arzerra, Aurexis, Avastin, Benlysta, Bexxar, Blontress, Bosatria, Campath, CEA-Cide, CEA-Scan, Cimzia, Cyramza, Ektomab, Erbitux, FibriScint, Gazyva, Herceptin, hPAM4-Cide, HumaSPECT, HuMax-CD4, HuMax-EGFr, Humira, HuZAF, Hybri-ceaker, Ilaris, Indimacis-125, Kadcyla, Lemtrada, LeukArrest, LeukoScan, Lucentis, Lymphomun, LymphoScan, LymphoStat-B, MabThera, Mycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Soliris, Stelara, Synagis, Tactress, Theracim, Theragyn, Theraloc, Tysabri, Vectibix, Verluma, Xolair, Yervoy, Zenapax, and Zevalin or combinations thereof.

Examples of known monoclonal antibodies include but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMG 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Deninituzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumab, Lanadelumab, Landogrozumab, Laprituximab emtansine, LBR-101/PF0442g7429, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Nam ilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox or combinations thereof.

Examples of vaccines developed for viral diseases include but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to: Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, *Yersinia pestis* vaccine; Examples of parasitic diseases include but are not limited to: Malaria vaccine, Schistosomiasis vaccine, Chagas disease vaccine, Hookworm vaccine, Onchocerciasis river blindness vaccine for humans, Trypanosomiasis vaccine, Visceral leishmaniasis vaccine; Examples of non-infectious diseases include but are not limited to: Alzheimer's disease amyloid protein vaccine, Breast cancer vaccine, Ovarian cancer vaccine, Prostate cancer vaccine, Talimogene laherparepvec (T-VEC); also vaccines including but not limited to the following trade names: ACAM2000, ActHIB, Adacel, Afluria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Flucelvax Quadrivalent, FluLaval, FluMist, FluMist Quadrivalent, Fluvirin, Fluzone Quadrivalent, Fluzone, Fluzone High-Dose and Fluzone Intradermal, Gardasil, Gardasil 9, Havrix, Hiberix, Imovax, Infanrix, IPOL, Ixiaro, JE-Vax, KINRIX, Menactra, Menhibrix, Menomune-A/C/WW-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TENIVAC, TICE BCG, Tripedia, TRUMENBA, Twinrix, TYPHIM Vi, VAQTA, Varivax, Vaxchora, Vivotif, YF-Vax, Zostavax, and combinations thereof.

Examples of injectable drugs include but are not limited to: Ablavar (Gadofosveset Trisodium Injection), Abarelix Depot, Abobotulinumtoxin A Injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab Injection), Acthrel (Corticorelin Ovine Triflutate for Injection), Actummune, Activase, Acyclovir for Injection (Zovirax Injection), [0137], Adacel, Adalimumab, Adenoscan (Adenosine Injection), Adenosine Injection (Adenoscan), Adrenaclick, AdreView (Iobenguane 1123 Injection for Intravenous Use), Afluria, Ak-Fluor (Fluorescein Injection), Aldurazyme (Laronidase), Alglucerase Injection (Ceredase), Alkeran Injection (Melphalan Hcl Injection), Allopurinol Sodium for Injection (Aloprim), Aloprim (Allopurinol Sodium for Injection), Alprostadil, Alsuma (Sumatriptan Injection), ALTU-238, Amino Acid Injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCI Injection (Amiodarone HCI Injection), Amobarbital Sodium Injection (Amytal Sodium), Amytal Sodium (Amobarbital Sodium Injection), Anakinra, Anti-Abeta, Anti-Beta7, Anti-Beta20, Anti-CD4, Anti-CD20, Anti-CD40, Anti-IFNalpha, Anti-IL13, Anti-OX4OL, Anti-oxLDS, Anti-NGF, Anti-NRP1, Arixtra, Amphadase (Hyaluronidase Inj), Ammonul (Sodium Phenylacetate and Sodium Benzoate Injection), Anaprox, Anzemet Injection (Dolasetron Mesylate Injection), Apidra (Insulin Glulisine [rDNA origin] Inj), Apomab, Aranesp (darbepoetin alfa), Argatroban (Argatroban Injection), Arginine Hydrochloride Injection (R-Gene 10, Aristocort, Aristospan, Arsenic Trioxide Injection (Trisenox), Articane HCl and Epinephrine Injection (Septocaine), Arzerra (Ofatumumab Injection), Asclera (Polidocanol Injection), Ataluren, Ataluren-DMD, Atenolol Inj (Tenorm in I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisodium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Altemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Carnitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Alfa Injection (Ovidrel), Cimzia, Cisplatin (Cisplatin Injection), Clolar (Clofarabine Injection), Clomiphine Citrate, Clonidine Injection (Duraclon), Cogentin (Benztropine Mesylate Injection), Colistimethate Injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin Injection), CF-101, Cyanokit (Hydroxocobalamin for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), Depo-Cyt (Cytarabine Liposome Injection), DepoDur (Morphine Sulfate XR Liposome Injection), Desmopressin Acetate Injection (DDAVP Injection), Depo-Estradiol, Depo-Provera 104 mg/ml, Depo-Provera 150 mg/ml, Depo-Testosterone, Dexrazoxane for Injection, Intravenous Infusion Only (Totect), Dextrose/Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eliglustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta), Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Flagyl Injection (Metronidazole Injection), Fluarix, Fludara (Fludarabine Phosphate), Fludeoxyglucose F 18 Injection (FDG), Fluorescein Injection (Ak-Fluor), Follistim AQ Cartridge (Follitropin Beta Injection), Follitropin Alfa Injection (Gonal-f RFF), Follitropin Beta Injection (Follistim AQ Cartridge), Folotyn (Pralatrexate Solution for Intravenous Injection), Fondaparinux, Forteo (Teriparatide (rDNA origin) Injection), Fostamatinib, Fosaprepitant Dimeglumine Injection (Emend Injection), Foscarnet Sodium Injection (Foscavir), Foscavir (Foscarnet Sodium Injection), Fosphenytoin Sodium Injection (Cerebyx), Fospropofol Disodium Injection (Lusedra), Fragm in, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disodium Injection (Eovist), Ganirelix (Ganirelix Acetate Injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatiramer Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humalog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Ilaris (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), Infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palm itate Extended-Release Injectable Suspension), Invirase (saquinavir mesylate), Iobenguane 1123 Injection for Intravenous Use (AdreView), Iopromide Injection (Ultravist), Ioversol Injection (Optiray Injection), Iplex (Mecasermin Rinfabate [rDNA origin] Injection), Iprivask, Irinotecan Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecallantide Injection), KCL in D5NS (Potassium Chloride in 5% Dextrose and Sodium Chloride Injection), KCL in D5W, KCL in NS, Kenalog 10 Injection (Triamcinolone Acetonide Injectable Suspension), Kepivance (Palifermin), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), lacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocarnitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for Injection (Repronex), Methohexital Sodium for Injection (Brevital Sodium), Methyldopate Hydrochloride Injection, Solution (Methyldopate Hcl), Methylene Blue (Methylene Blue Injection), Methylprednisolone Acetate Injectable Suspension (Depo Medrol), MetMab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium Injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR Inj (Vivitrol), Naprosyn (naproxen), NeoProfen (Ibuprofen Lysine Injection), Nandrol Decanoate, Neostigmine Methylsulfate (Neostigmine Methylsulfate Injection), NEO-GAA, NeoTect (Technetium Tc 99m Depreotide Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCI Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprevv), Omnitarg, Omnitrope (Somatropin [rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pamidronate Disodium Injection (Pamidronate Disodium Injection), Panitumumab Injection for Intravenous Use (Vectibix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGlntron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Plasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Asclera), Potassium Chloride, Pralatrexate Solution for Intravenous Injection (Folotyn), Pramlintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCI Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renagel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Istodax), Saizen (Somatropin Injection), Sandostatin LAR (Octreotide Acetate Injection), Sclerostin Ab, Sensipar (cinacalcet), Sensorcaine (Bupivacaine HCl Injections), Septocaine (Articane HCI and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox Injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intra-articular Injection), Tarceva, Taxotere (Docetaxel for Injection), Technetium Tc 99m, Telavancin for Injection (Vibativ), Temsirolimus Injection (Torisel), Tenorm in I.V. Injection (Atenolol Inj), Teriparatide (rDNA origin) Injection (Forteo), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Galaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Trioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Valproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofosveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (lacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR Inj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprevv (Olanzapine Extended Release Injectable Suspension) and combinations thereof.

Test Methods

It should be understood that although certain methods and equipment are described below, other methods or equipment determined suitable by one of ordinary skill in the art may be alternatively utilized.

Helium Leak

To evaluate the seal of the plunger to the barrel the leak rate of helium from the internals of an assembled syringe system to the external environment was performed. This was accomplished by placing a stopper into a dry bare glass barrel (no lubricant present) and restraining the plunger rod to prevent movement of the stopper during testing. The internal volume of the assembled syringe was evacuated through the needle by use of a vacuum and replaced with a helium atmosphere pressurized to approximately 1 psig. The space around the syringe was monitored by use of a Mass Spectrometer (MS) tuned for helium (LACO's TitanTest™ Helium Leak Tester, Salt Lake City, UT). The area around the syringe was evacuated and analyzed for Helium concentration to determine a helium leak rate at 30 seconds after helium differential pressure of approximately 15.7 psig was established.

Contact Angle Measurement

Water contact angles of the glass barrels were measured by cutting both ends off a syringe and measuring a sessile drop at each end using a Kruss (Hamburg, Germany) DSA100 goniometer. The contact angle was taken as the angle between the tangent of the drop and the tangent of the glass barrel.

Slide Force

Slide force was measured by filling syringe with 0.96 ml of Water For Injection (WFI) and inserting stopper using a vent tube stopper insertion machine. The syringe used was a staked needle design with a 25-31 gauge by 0.25-1 inch needle. After filling, the syringe was allowed to sit for approximately 24 hours, after which, an appropriate plunger rod to match the stopper was fitted into the assembled syringe system without moving or disturbing the stopper. The system was placed into a holder on a force displacement analyzer and the cross head moved at a rate of 25 mm/minute until contact was made between the crosshead and the plunger rod proximal end. The test speed of 250 mm/minute was established and data was recorded approximately every 0.005 seconds, after which force displacement data was obtained. The force displacement instrument used was a TA XT Plus Texture Analyzer with a TA-270N syringe test fixture (Hamilton, Mass.).

Break Loose Force is the maximum slide force recorded between 0 and 3 mm displacement for a 1 ml long syringe.

Average Glide Force is the average slide force recorded between 10 and 28 mm displacement for a 1 ml long syringe.

Glide Force Variation was calculated from the slide force measurements between 10 and 28 mm for a 1 ml long syringe. Specifically, the squares of the differences between each point and the average glide force are summed and then divided by the number of data points between 10 and 28 mm for a 1 ml long syringe. Finally the square root of this value is calculated. The equation is presented below.

$$\text{Glide Force Variation} = \sqrt{\frac{\sum_{i=1}^{n} (x_i - AGF)^2}{n}}$$

$x_i$=Force measurement of a data point between 10 and 28 mm for a 1 ml long syringe.

AGF=Average Glide Force.

n=The number of data points between 10 and 28 mm for a 1 ml long syringe.

Contact Width

The contact width of the plunger interface with a glass barrel was measured under 30× magnification averaging 3 measurements on each rib using a Keyence digital microscope VHX-5000 (Itasca, IL).

Barrel Inner Diameter (ID)

The inner diameter of the syringe barrel was measured by use of a digital three point internal micrometer (Mitutoyo series 468, Aurora, Illinois).

EXAMPLES

The syringe barrel, needle gauges, and needle lengths disclosed are exemplary and not limiting to the scope of this invention. Additionally, the stoppers can be scaled to fit various barrel sizes. The barrels may have any diameter and length as long as the stopper described previously is scaled appropriately to fit the diameter of the barrel. Typical syringe barrels include but are not limited to 0.5 ml, 1 ml long, 1-3 ml standard, 5 ml, 10 ml, 20 ml, 50 ml, and 100 ml. Furthermore, the barrel may be composed of plastic, a polymeric material, glass that has been treated to have a hydrophobic inner surface, or other suitable materials such Example 8 in Table 1 is an example of a stopper with a compression value greater than about 7.9% and sliding surface less than about 2.0 mm with low glide force variation.

Examples 9 and 10 in Table 1 are examples of stoppers with a compression value between about 4.5% and about 7.9% and a sliding surface from about 2 mm to about 3.2 mm, and which show acceptable seal, acceptable break force, acceptable glide force, and low glide force variation.

TABLE 1

| Sample | Barrel ID (mm) | Barrel contact angle | Compression (Rib 1) (%) | Sliding Surface (mm) | He leak rate (sccs) | Maximum extrusion (break loose) force (N) | Average Glide Force (N) | Glide Force Variation (N) |
|---|---|---|---|---|---|---|---|---|
| Example 1 | 6.34 | 96° | 4.50 | 0.37 | $1.10 \times 10^{-6}$ | 3.1 | 2.3 | 0.087 |
| Example 2 | 6.34 | 96° | 2.85 | 0.56 | $6.8 \times 10^{-6}$ | 2.2 | 2.2 | 0.107 |
| Example 3 | 6.34 | 96° | 4.53 | 0.52 | $1.44 \times 10^{-6}$ | 2.4 | 2.1 | 0.069 |
| Example 4 | 6.34 | 96° | 7.67 | 0.40 | $4.5 \times 10^{-7}$ | 3.8 | 3.1 | 0.792 |
| Example 5 | 6.34 | 96° | 5.12 | 1.59 | $2.8 \times 10^{-7}$ | 3.0 | 2.6 | 0.052 |
| Example 6 | 6.34 | 96° | 12.30 | 2.00 | $5.9 \times 10^{-10}$ | 11.4 | 7.6 | 0.133 |
| Example 7 | 6.34 | 96° | 8.29 | 2.38 | $1.10 \times 10^{-8}$ | 5.9 | 4.4 | 0.057 |
| Example 8 | 6.34 | 96° | 14.56 | 1.06 | $2.4 \times 10^{-7}$ | 8.3 | 5.3 | 0.198 |
| Example 9 | 6.34 | 96 | 5.57 | 2.17 | $1.57 \times 10^{-6}$ | 6.8 | 3.7 | 0.095 |
| Example 10 | 6.34 | 96 | 6.04 | 2.78 | $1.07 \times 10^{-6}$ | 7.1 | 5.3 | 0.217 | as those described herein. The needle may be any gauge commonly used for injections. Typical needle gauges are in the range of 25G to 34G.

Examples 1-10

A series of stoppers was fabricated as described in U.S. Pat. No. 8,722,178 to Ashmead, et al. using a halobutyl rubber with an initial modulus of 3.5 MPa. The stoppers were sized for use with a 1 ml long glass barrel with a nominal inside diameter of 6.35 mm. The stoppers differed in number, shape and size of the ribs intended to form the seal against the interior of the syringe barrel. After processing was completed, the stopper (i.e., Examples 1-10) was measured using non-contact measuring equipment. The stoppers were washed using warm purified water with a small amount of detergent, then rinsed and dried to remove any residual contamination from fabrication. For Examples 1-10, lubricant-free glass barrels (SyriQ®, part number 1509955, 27GX ½" needle, commercially available from Schott, USA) were coated with a nominally 5 µm thick layer of Parylene HT (Specialty Coating Systems, Indianapolis, Ind.) to create a hydrophobic surface. The stoppers were inserted into the coated glass barrels and tested as described herein. The results are reported in Table 1. Rib 1 is the distal end rib and subsequent ribs count up towards the proximal end.

Examples 1, 3, 4 and 5 in Table 1 are examples of stoppers that have compression values less than about 7.9% and show acceptable seal, low break force, low glide force, and low glide force variation.

Example 2 in Table 1 is an example of a stopper which has low glide force and low glide force variation but is insufficient in diameter to achieve the required seal and is therefore insufficient.

Examples 6 and 7 in Table 1 are examples of stoppers with compression values less than about 7.9% and sliding surfaces of greater than or equal to 2.0 mm showing acceptable seal, acceptable break loose force and low glide force variation.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical delivery device comprising:
    a barrel having an inner surface; and
    a stopper contacting at least a portion of the inner surface of the barrel; said stopper having a compressibility between about 4.5% to about 7.9% measured against said barrel,
    wherein said inner surface of barrel has a water contact angle greater than 90°,
    wherein the stopper has a sliding surface less than about 2 mm, and
    wherein the stopper has a glide force variation less than about 1.3 N when calculated according to the Glide Force Variation test method.

2. The medical delivery device of claim 1, wherein said inner surface of the barrel has a water contact angle between 96° and about 120°.

3. The medical delivery device of claim 1, wherein said inner surface is free or substantially free of lubricants.

4. The medical delivery device of claim 1, wherein said stopper is covered with one or more fluoropolymer layers.

5. The medical delivery device of claim 4, wherein the one or more fluoropolymer layers comprise a composite material having a barrier layer and a porous layer, the barrier layer comprising at least one member selected from the group consisting of densified expanded polytetrafluoroethylene, expanded polytetrafluoroethylene, polytetrafluoroethylene, fluorinated ethylene propylene, polyethylene, polypropylene, polyvinylidene fluoride, polyvinylfluoride, perfluoropropylevinylether, Parylene AF-4, Parylene VT-4, Parylene C, Parylene N, a perfluoroalkoxy polymer, and copolymers and combinations thereof.

6. The medical delivery device of claim 4, wherein said one or more fluoropolymer layers comprise densified expanded polytetrafluoroethylene or expanded polytetrafluoroethylene.

7. The medical delivery device of claim 1, wherein stopper has a break loose force less than about 7 N.

8. The medical delivery device of claim 1, wherein the stopper has an average glide force less than about 4 N.

9. A medical delivery device comprising:
a barrel having an inner surface; and
a stopper contacting at least a portion of the inner surface of the barrel; said stopper having a compressibility between about 4.5% to 7.9% measured against said barrel,
wherein said inner surface of barrel has a water contact angle greater than 90°.
wherein the stopper has a sliding surface less than about 2 mm, and wherein the stopper has an average glide force less than about 4 N.

10. The medical delivery device of claim 9, wherein said inner surface of the barrel has a water contact angle between 96° and about 120°.

11. The medical delivery device of claim 9, wherein said inner surface is free or substantially free of lubricants.

12. The medical delivery device of claim 9, wherein said stopper is covered with one or more fluoropolymer layers.

13. The medical delivery device of claim 12, wherein the one or more fluoropolymer layers comprise a composite material having a barrier layer and a porous layer, the barrier layer comprising at least one member selected from the group consisting of densified expanded polytetrafluoroethylene, expanded polytetrafluoroethylene, polytetrafluoroethylene, fluorinated ethylene propylene, polyethylene, polypropylene, polyvinylidene fluoride, polyvinylfluoride, perfluoropropylevinylether, Parylene AF-4, Parylene VT-4, Parylene C, Parylene N, a perfluoroalkoxy polymer, and copolymers and combinations thereof.

14. The medical delivery device of claim 12, wherein said one or more fluoropolymer layers comprise densified expanded polytetrafluoroethylene or expanded polytetrafluoroethylene.

15. The medical delivery device of claim 9, wherein stopper has a break loose force less than about 7 N.

16. The medical delivery device of claim 9, wherein the stopper includes two or more sealing ribs.

* * * * *